(12) United States Patent  
Fukushi et al.

(10) Patent No.: US 12,150,756 B2  
(45) Date of Patent: Nov. 26, 2024

(54) FOOT ANGLE CALCULATION

(71) Applicant: NEC Corporation, Tokyo (JP)

(72) Inventors: Kenichiro Fukushi, Tokyo (JP); Chenhui Huang, Tokyo (JP); Zhenwei Wang, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

(21) Appl. No.: 17/766,327

(22) PCT Filed: Oct. 30, 2019

(86) PCT No.: PCT/JP2019/042516  
§ 371 (c)(1),  
(2) Date: Apr. 4, 2022

(87) PCT Pub. No.: WO2021/084641  
PCT Pub. Date: May 6, 2021

(65) Prior Publication Data  
US 2024/0049990 A1 Feb. 15, 2024

(51) Int. Cl.  
A61B 5/11 (2006.01)  
A61B 5/00 (2006.01)

(52) U.S. Cl.  
CPC ............ *A61B 5/1121* (2013.01); *A61B 5/112* (2013.01); *A61B 5/742* (2013.01); *A61B 5/6807* (2013.01); *A61B 2562/0219* (2013.01)

(58) Field of Classification Search  
CPC ....... A61B 5/1121; A61B 5/742; A61B 5/112; A61B 2562/0219; A61B 5/6807  
See application file for complete search history.

(56) References Cited

U.S. PATENT DOCUMENTS

| 7,991,508 | B2* | 8/2011 | Hasegawa | B62D 57/032 |
| | | | | 700/260 |
| 9,759,567 | B2* | 9/2017 | Sato | G01C 22/006 |
| 2014/0303924 | A1 | 10/2014 | Kumar et al. | |
| 2021/0247189 | A1* | 8/2021 | Tsujii | G01C 22/006 |
| 2021/0401325 | A1* | 12/2021 | Fukushi | A61B 5/112 |

FOREIGN PATENT DOCUMENTS

| JP | 2013-088280 A | 5/2013 |
| JP | 2015-217250 A | 12/2015 |
| JP | 2016-202381 A | 12/2016 |
| JP | 6299147 82 | 3/2018 |
| JP | 2019-005340 A | 1/2019 |
| WO | 2018/033965 | 2/2018 |

OTHER PUBLICATIONS

International Search Report for PCT Application No. PCT/JP2019/042516, mailed on Jan. 7, 2020.  
English translation of Written opinion for PCT Application No. PCT/JP2019/042516, mailed on Jan. 7, 2020.  
S. Madgwick, A. Harrison, R. Vaidyanathan, "Estimation of IMU and MARG orientation using a gradient descent algorithm," 2011 IEEE International Conference on Rehabilitation Robotics, Rehab Week Zurich, ETH Zurich Science City, Switzerland, Jun. 29-Jul. 1, pp. 179-185, 2011.

* cited by examiner

*Primary Examiner* — An H Do

(57) ABSTRACT

A foot angle calculation device including: a posture angle calculation unit that calculates a posture angle by using an angular velocity vector of a foot portion; and a foot angle calculation unit that calculates a foot angle that is an angle formed by a velocity vector of the foot portion and a center line of a foot by using the velocity vector and the posture angle.

8 Claims, 20 Drawing Sheets

MEDIAL ROTATION

LATERAL ROTATION

FOOT ANGLE CALCULATION

This application is a National Stage Entry of PCT/JP2019/042516 filed on Oct. 30, 2019, the contents of all of which are incorporated herein by reference, in their entirety.

TECHNICAL FIELD

The present invention relates to a gait measurement system and the like for measuring a gait of a pedestrian.

BACKGROUND ART

With increasing interest in healthcare for physical condition management, a technique for measuring a gait including the feature of walking of a pedestrian has been developed.

NPL 1 discloses a method for calculating a posture angle of a foot of a pedestrian by using acceleration data measured by an inertial measurement unit (IMU).

PTL 1 discloses a displaying method of a walking feature which displays the evaluation result of the walking feature of a subject on a display. In the method of PTL 1, walking parameters including a walking factor obtained by walking trace measurement are acquired from a plurality of subjects, and a plurality of main components obtained by standardizing the walking parameters and performing main component analysis are acquired as evaluation axes of the walking feature. Then, in the method of PTL 1, the walking parameters including the walking factor measured from the walking trace of a random subject are used to evaluate the walking feature of the subject on the evaluation axes in a plurality of stages, and the moving image of a footprint image is created as the evaluation result based on the evaluation stages.

PTL 2 discloses an analysis system that analyzes the behavior of a lower leg portion including a lower leg and a foot. The analysis system of PTL 2 derives analysis information regarding the behavior of the lower leg portion based on relative angle information indicating the degree of inclination of the heel to the inside and outside with respect to the lower leg and tilt angle information indicating the degree of inclination of the heel to the inside and outside with respect to the ground of the foot.

PTL 3 discloses a reference value generation method for generating a reference value for correcting any of detection values of posture, velocity, angular velocity, and acceleration. In the method of PTL 3, the detection value detected during the user's travel period is stored in a storage unit, the transition portion of the past detection value similar to the transition of the detection value up to the present is extracted from the storage unit, and the reference value is generated by using the extraction result.

CITATION LIST

Patent Literature

[PTL 1] Japanese Patent No. 6299147
[PTL 2] WO 2018/033965 A
[PTL 3] JP 2013-088280 A

Non Patent Literature

[NPL 1] S. Madgwick, A. Harrison, R. Vaidyanathan, "Estimation of IMU and MARG orientation using a gradient descent algorithm," 2011 IEEE International Conference on Rehabilitation Robotics, Rehab Week Zurich, ETH Zurich Science City, Switzerland, June 29-July 1, pp. 179-185, 2011.

SUMMARY OF INVENTION

Technical Problem

According to the method of PTL 1, the walking feature is briefly evaluated by using the walking trace of the subject, and the evaluation result indicating the walking feature of the subject can be displayed on a screen in an easy-to-understand manner. However, in the method of PTL 1, it is necessary to detect the walking trace with a seat type pressure sensor in order to measure an angle (hereinafter, referred to as a foot angle) formed by the traveling direction of the pedestrian and the center line of the foot as the gait of the pedestrian, and a large-scale device is required.

According to the system of PTL 2, the behavior of the lower leg portion including the calf and the foot can be analyzed. However, in the system of PTL 2, it is necessary to analyze the image captured by a camera in order to measure the foot angle, and the foot angle is not easily measured.

According to the method of PTL 3, the reference value can be generated by extracting the transition portion of the past detection value similar to the transition of the detection value up to the present from the storage unit. However, in the method of PTL 3, when the transition portion of the past detection value similar to the transition of the detection value up to the present is not stored in the storage unit, the measurement error of the detection value cannot be corrected.

An object of the present invention is to solve the above-described problems and to provide a foot angle calculation device and the like capable of easily measuring a foot angle of a pedestrian with high accuracy.

Solution to Problem

A foot angle calculation device according to one aspect of the present invention includes: a posture angle calculation unit configured to calculate a posture angle by using an angular velocity vector of a foot portion; and a foot angle calculation unit configured to calculate a foot angle that is an angle formed by a velocity vector of the foot portion and a center line of a foot by using the velocity vector and the posture angle.

In a gait measurement method according to one aspect of the present invention, a computer executes the method including: calculating a posture angle by using an angular velocity vector of a foot portion; and calculating a foot angle that is an angle formed by a velocity vector of the foot portion and a center line of a foot by using the velocity vector and the posture angle.

A program according to one aspect of the present invention causes a computer to execute a process including: calculating a posture angle by using an angular velocity vector of a foot portion; and calculating a foot angle that is an angle formed by a velocity vector of the foot portion and a center line of a foot by using the velocity vector and the posture angle.

Advantageous Effects of Invention

According to the present invention, it is possible to provide the foot angle calculation device and the like capable of easily measuring the foot angle of the pedestrian with high accuracy.

EXAMPLE EMBODIMENT

Figure 1:
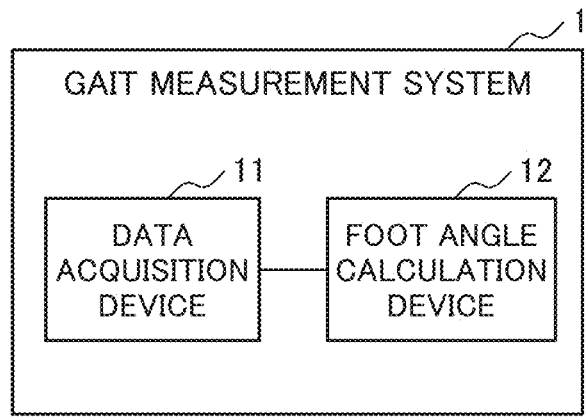
FIG. 1 is a block diagram illustrating an example of a configuration of a gait measurement system according to a first example embodiment of the present invention.

Hereinafter, example embodiments of the present invention will be described with reference to the drawings. However, the example embodiments described below have technically preferable limitations for carrying out the present invention, but the scope of the invention is not limited to the following. In all the drawings used in the following description of the following example embodiments, the same reference numerals are given to the same parts unless there is a particular reason. In the following example embodiments, repeated description of similar configurations and operations may be omitted. The directions of arrows in the drawings illustrate an example, and do not limit the directions of signals between blocks and the like. In the following example embodiments, a vector is written in a normal font without using bold letters or arrows.

First Example Embodiment

First, a gait measurement system according to a first example embodiment of the present invention will be described with reference to the drawings. The gait measurement system of the present example embodiment includes a foot angle calculation device that calculates an angle (hereinafter, referred to as a foot angle) formed by a traveling direction of a pedestrian and a center line of a foot by using sensor data acquired by a sensor arranged on footwear such as shoes. In a case where the pedestrian is walking along a curve or walking in a meandering manner, there is a situation where an accurate foot angle cannot be calculated since the traveling direction of the pedestrian changes in a period from stepping-out of the foot to landing. Therefore, in the present example embodiment, the velocity vector of the foot of the pedestrian is regarded as the traveling direction of the pedestrian in such a way that the accurate foot angle can be calculated even when the pedestrian is not walking straight. That is, the foot angle calculation device according to the present example embodiment calculates, as the foot angle, an angle formed by the velocity vector of the foot of the pedestrian and the center line of the foot. In the following, an example will be described in which the foot angle calculation device calculates the velocity vector and a posture angle by using sensor data acquired by an acceleration sensor and an angular velocity sensor arranged on the footwear, and calculates the foot angle by using the calculated velocity vector and posture angle.

Configuration

FIG. 1 is a block diagram illustrating an outline of a configuration of a gait measurement system 1 of the present example embodiment. The gait measurement system 1 includes a data acquisition device 11 and a foot angle calculation device 12. The data acquisition device 11 and the foot angle calculation device 12 may be connected by wire or may be connected wirelessly. The data acquisition device 11 and the foot angle calculation device 12 may be configured by a single device. The data acquisition device 11 may be removed from the configuration of the gait measurement system 1, and the gait measurement system 1 may be configured only by the foot angle calculation device 12.

The data acquisition device 11 is connected to the foot angle calculation device 12. The data acquisition device 11 includes at least an acceleration sensor and an angular velocity sensor. For example, the data acquisition device 11 is installed on the footwear of a user. The data acquisition device 11 converts physical quantities such as an acceleration and an angular velocity acquired by the acceleration sensor and the angular velocity sensor into digital data (also referred to as sensor data), and transmits the converted sensor data to the foot angle calculation device 12.

The data acquisition device 11 is achieved by, for example, an inertial measurement device including the acceleration sensor and the angular velocity sensor. An example of the inertial measurement device includes an inertial measurement unit (IMU). The IMU includes a three-axis acceleration sensor and a three-axis angular velocity sensor. An example of the inertial measurement device is a vertical gyro (VG). The VG has a configuration similar to that of the IMU, and can output a roll angle and a pitch angle with reference to a gravity direction by a method called strapdown. An example of the inertial measurement device includes an attitude heading reference system (AHRS). The AHRS has a configuration in which an electronic compass is added to the VG. The AHRS can output a yaw angle in addition to the roll angle and the pitch angle. An example of the inertial measurement device includes a global positioning system/inertial navigation system (GPS/INS). The GPS/INS has a configuration in which a GPS is added to the AHRS. Since the GPS/INS can calculate a position in a three-dimensional space in addition to the roll angle, the pitch angle, and the yaw angle, the position can be estimated with high accuracy.

Figure 2:
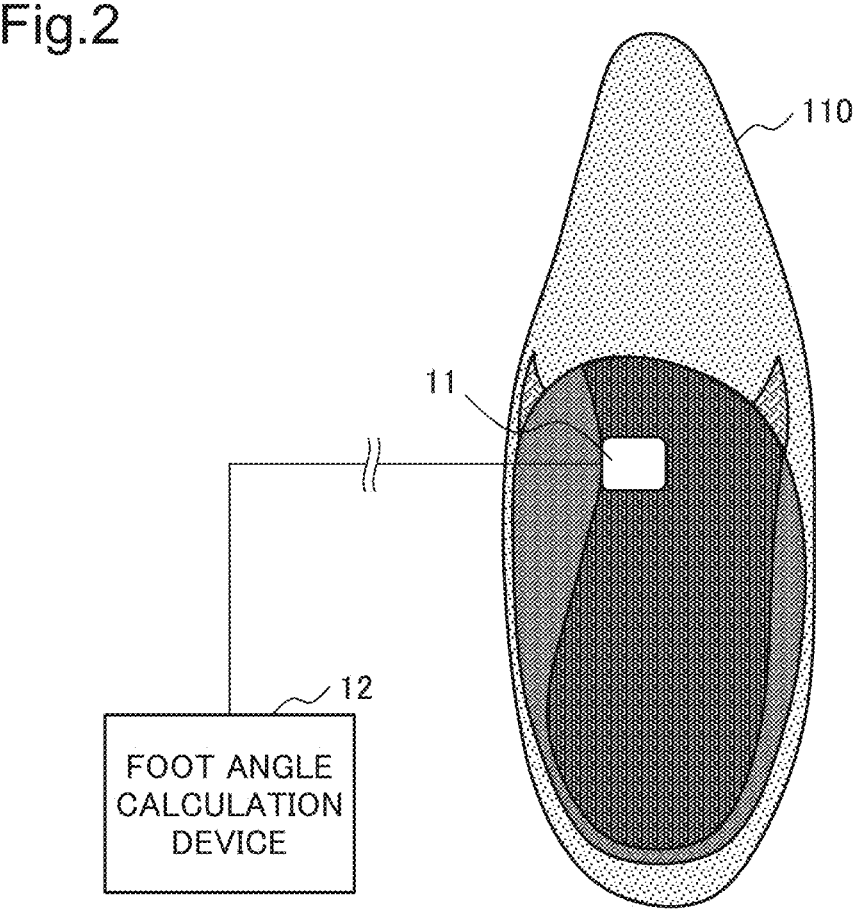
FIG. 2 is a conceptual diagram illustrating an arrangement example of a data acquisition device of the gait measurement system according to the first example embodiment of the present invention.

FIG. 2 is a conceptual diagram illustrating an example in which the data acquisition device 11 is installed in a shoe 110. In the example of FIG. 2, the data acquisition device 11 is installed at a position facing the back side of the arch of the foot. The position where the data acquisition device 11 is installed may be a position other than the back side of the arch of the foot as long as the position is inside or on the surface of the shoe 110. For example, the data acquisition device 11 may be installed on the back side of a toe or a heel.

Figure 3:
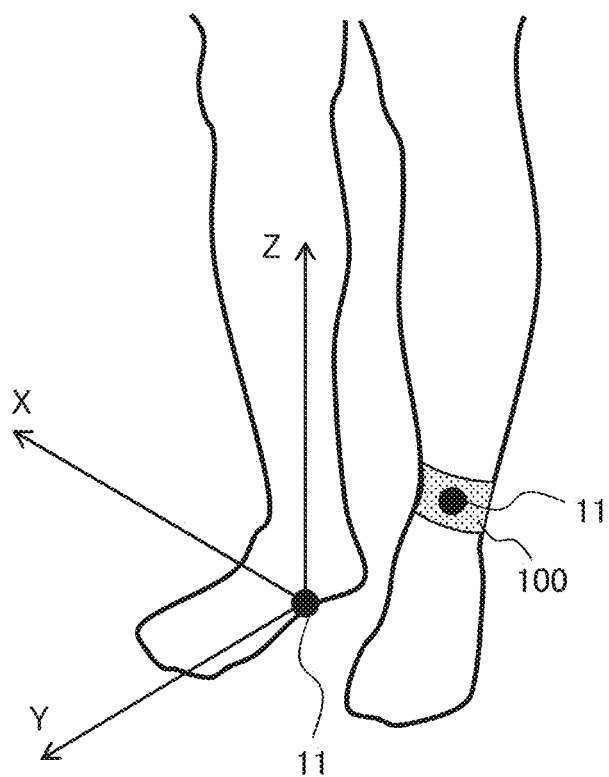
FIG. 3 is a conceptual diagram for describing a coordinate system of sensor data acquired by the gait measurement system according to the first example embodiment of the present invention.

FIG. 3 is a conceptual diagram for describing a coordinate system (X axis, Y axis, Z axis) set in the data acquisition device 11 in a case where the data acquisition device 11 is installed on the back side of the arch of the foot. FIG. 3 illustrates an example in which the lateral direction of the pedestrian is set to an X-axis direction (a rightward direction is positive), the traveling direction of the pedestrian is set to the Y-axis direction (a forward direction is positive), and the gravity direction is set to a Z-axis direction (a vertically upward direction is positive). The data acquisition device 11 may be configured to be attached to an ankle or a foot. FIG. 3 illustrates an example in which the data acquisition device 11 is fixed by a band 100 at the position of the ankle of a left foot. For example, the data acquisition device 11 may be fixed to the position of the ankle or the foot by a sock, a supporter, or the like. FIG. 3 illustrates that the data acquisition device 11 is installed at the back side of the arch of a right foot and the position of the ankle of the left foot, but does not illustrate that the data acquisition device 11 is installed at both the back side of the arch of the right foot and the position of the ankle of the left foot. Usually, the data acquisition device 11 is preferably installed at the same position in the left and right feet or ankles.

The foot angle calculation device 12 receives sensor data from the data acquisition device 11. The foot angle calculation device 12 calculates a foot angle by using the received sensor data. More specifically, the foot angle calculation device 12 calculates a velocity vector by time-integrating an acceleration vector, calculates a posture angle by using an angular velocity vector, and calculates the foot angle by using the velocity vector and the posture angle.

Figure 4:
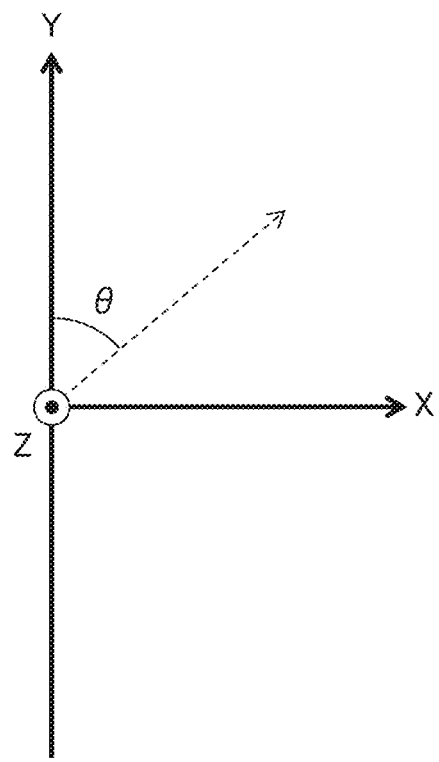
FIG. 4 is a conceptual diagram for describing a coordinate system of a posture angle calculated by the gait measurement system according to the first example embodiment of the present invention.

FIG. 4 is a conceptual diagram for describing a coordinate system of the posture angle calculated by the foot angle calculation device 12. In the present example embodiment, the posture angle indicates a rotation angle of a foot in a plane of a floor plane (also referred to as a horizontal plane) centered on an axis (Z axis) in the gravity direction. In FIG. 4, the posture angle is an angle θ formed by the traveling direction (the positive direction of the Y axis) of the pedestrian and the center line (broken line arrow) of the foot with the axis (Z axis) of the gravity direction as the center.

For example, the foot angle calculation device 12 generates time-series data of the posture angle. For example, the foot angle calculation device 12 generates time-series data of the posture angle at a predetermined timing or time interval set in accordance with a general gait cycle or a gait cycle unique to the user. For example, the foot angle calculation device 12 continues to generate the time-series data of the posture angle during a period in which the walking of the user is continued. The timing at which the foot angle calculation device 12 generates the time-series data of the posture angle can be randomly set. The foot angle calculation device 12 may be configured to measure an acceleration or an angular velocity at a specific time.

By integrating the value of the angular velocity having each of the X axis, the Y axis, and the Z axis as a central axis, the foot angle calculation device 12 can calculate the posture angle around the axes. The angular velocity data includes an error mainly caused by bias. The error included in the angular velocity data is accumulated by integration. Therefore, the posture angle may be calculated using the acceleration data by a method of Madgwick disclosed in NPL 1 below. According to the method of Madgwick, accumulation of errors can be reduced by integrating and using the measurement data of the angular velocity and the measurement data of the acceleration with reference to the gravitational acceleration.

NPL 1: S. Madgwick, A. Harrison, R. Vaidyanathan, "Estimation of IMU and MARG orientation using a gradient descent algorithm," 2011 IEEE International Conference on Rehabilitation Robotics, Rehab Week Zurich, ETH Zurich Science City, Switzerland, June 29-July 1, pp. 179-185, 2011.

The acceleration data and the angular velocity data include high-frequency and low-frequency noises that change in various directions. Therefore, by applying a low-pass filter and a high-pass filter to the acceleration data and the angular velocity data to remove a high-frequency component and a low-frequency component, it is possible to improve the accuracy of sensor data from a foot portion where noise easily interferes. By applying a complementary filter to each of the acceleration data and the angular velocity data and taking a weighted average, the accuracy of sensor data can be improved.

Figure 5:
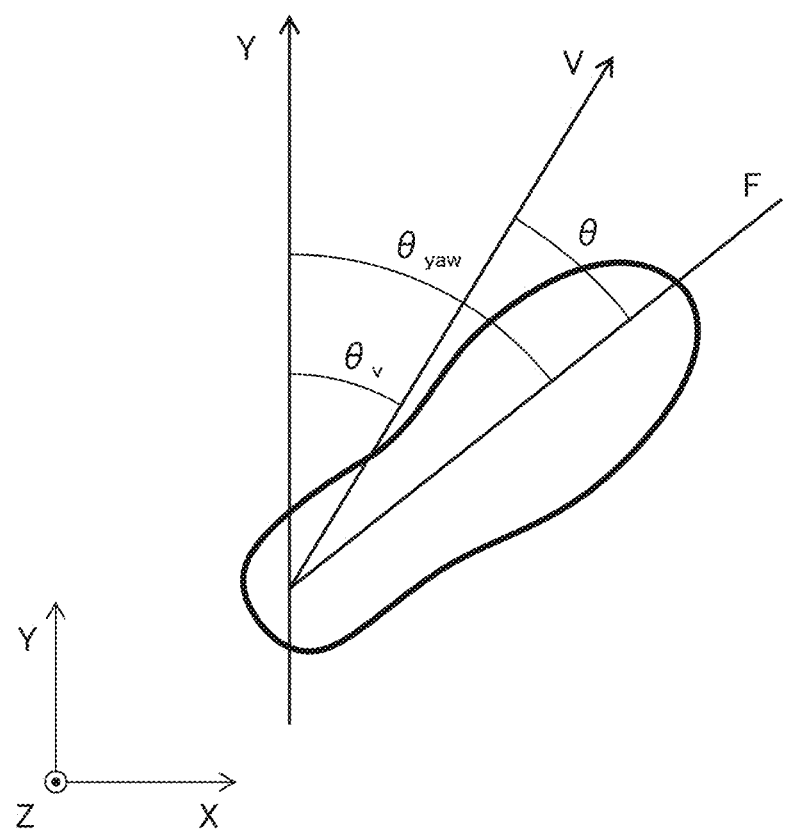
FIG. 5 is a conceptual diagram for describing a foot angle calculated by the gait measurement system according to the first example embodiment of the present invention.

FIG. 5 is a conceptual diagram for describing the foot angle calculated by the foot angle calculation device 12 in a case where the data acquisition device 11 is installed on the right foot. The Y axis is an axis indicating the traveling direction in the coordinate system set in the data acquisition device 11. V indicates the direction of the velocity vector calculated using the acceleration vector acquired by the data acquisition device 11. F indicates a direction along the center line of the foot. For example, the center line F of the foot can be defined by a straight line connecting the center of the index finger of the foot and the center of the heel. The center line F of the foot only needs to define the direction of the foot, and is not limited to the straight line connecting the center of the index finger of the foot and the center of the heel.

A yaw angle $\theta_{yaw}$ is an angle formed by the center line F of the foot and the Y axis. The yaw angle $\theta_{yaw}$ is measured by the data acquisition device 11. A velocity angle $\theta_v$ is an angle formed by a velocity vector V and a Y axis on the floor plane. The foot angle calculation device 12 calculates a velocity angle $\theta_v$ by using following Equation 1.

$$\theta_v = \tan^{-1}\frac{v_X}{v_Y} \qquad (1)$$

In Equation 1 described above, $v_x$ is an X component of the velocity vector V, and $v_y$ is a Y component of the velocity vector V.

The foot angle $\theta$ is an angle formed by the velocity vector V and the center line F of the foot. In other words, the foot angle $\theta$ indicates the rotation angle of the center line F of the foot about the Z axis in a case where the direction of the velocity vector V is 0 degrees. The foot angle calculation device 12 calculates the foot angle $\theta$ by using following Equation 2.

$$\theta = \theta_{yaw} - \theta_v \qquad (2)$$

In Equation 2 described above, a clockwise direction with respect to the Z axis is positive, and a counterclockwise direction with respect to the Z axis is negative.

Figure 6:
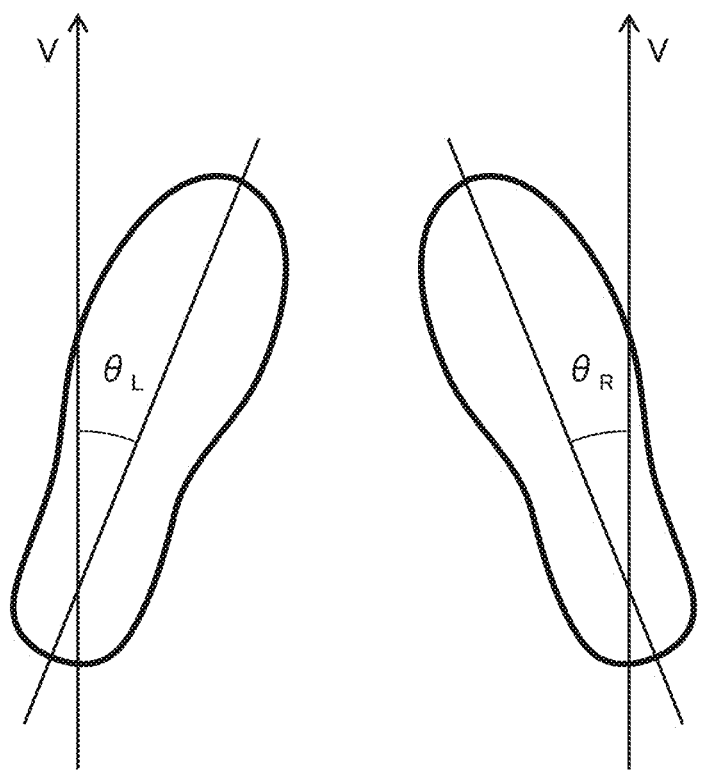
FIG. 6 is a conceptual diagram for describing an example of a foot angle calculated by the gait measurement system according to the first example embodiment of the present invention.
Figure 7:
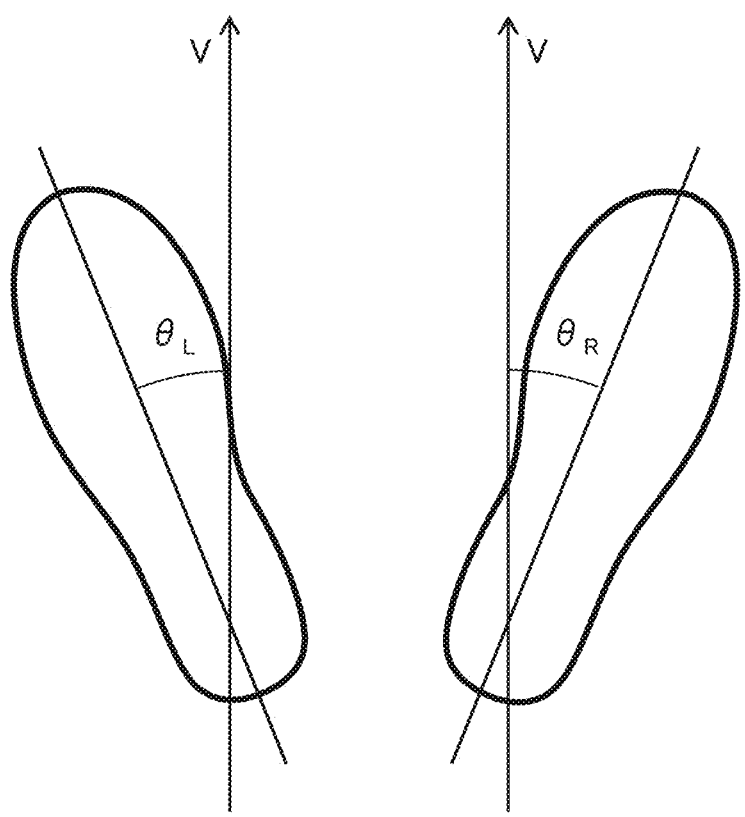
FIG. 7 is a conceptual diagram for describing another example of the foot angle calculated by the gait measurement system according to the first example embodiment of the present invention.

FIGS. 6 and 7 are conceptual diagrams for describing an example of the foot angle of the pedestrian. In FIGS. 6 and 7, the foot angle of the left foot is denoted as $\theta_L$, and the foot angle of the right foot is denoted as $\theta_R$. In the examples of FIGS. 6 and 7, it is assumed that the data acquisition devices 11 are installed on both feet. In the case of evaluating the foot angle of one foot, it is sufficient if the data acquisition device 11 is be installed in the foot to be evaluated. Hereinafter, an example in which the coordinate systems of the right foot and the left foot are the same will be described, but the coordinate systems of the right foot and the left foot may be different.

FIG. 6 illustrates an example in which the pedestrian walks with feet turned in. In the case of the medial rotation of the feet as illustrated in FIG. 6, the foot angle $\theta_L$ of the left foot is positive, and the foot angle $\theta_R$ of the right foot is negative. That is, when the foot angle $\theta_L$ of the left foot is positive, and the foot angle $\theta_R$ of the right foot is negative, it can be determined that the pedestrian is walking with feet turned in.

FIG. 7 illustrates an example in which the pedestrian walks with feet turned out. In the case of the lateral rotation of the feet rotate as illustrated in FIG. 7, the foot angle $\theta_L$ of the left foot is negative, and the foot angle $\theta_R$ of the right foot is positive. That is, when the foot angle $\theta_L$ of the left foot is negative, and the foot angle $\theta_R$ of the right foot is positive, it can be determined that the pedestrian is walking with feet turned out.

The foot angle calculation device 12 outputs information regarding the calculated foot angle. For example, the foot angle calculation device 12 outputs the data value of the calculated foot angle. For example, the foot angle calculation device 12 outputs information regarding the foot angle to a display device (not illustrated). For example, the foot angle calculation device 12 outputs information regarding the foot angle to a system or a device (not illustrated) that measures the number of steps and the gait based on based on the data value of the foot angle. The output target of the information regarding the foot angle is not particularly limited as long as the target is a system or a device using the information.

The foot angle calculation device 12 is achieved by, for example, software (application) installed in a portable terminal device such as a smartphone, a mobile phone, a tablet, or a notebook personal computer, or a circuit. For example, the foot angle calculation device 12 may be achieved by software installed in an information processing device such as a stationary computer or a server, or a circuit.

The outline of the configuration of the gait measurement system 1 of the present example embodiment has been described above. The configuration of FIG. 1 is an example, and the gait measurement system 1 of the present example embodiment is not limited to the configuration of FIG. 1.

Data Acquisition Device

Figure 8:
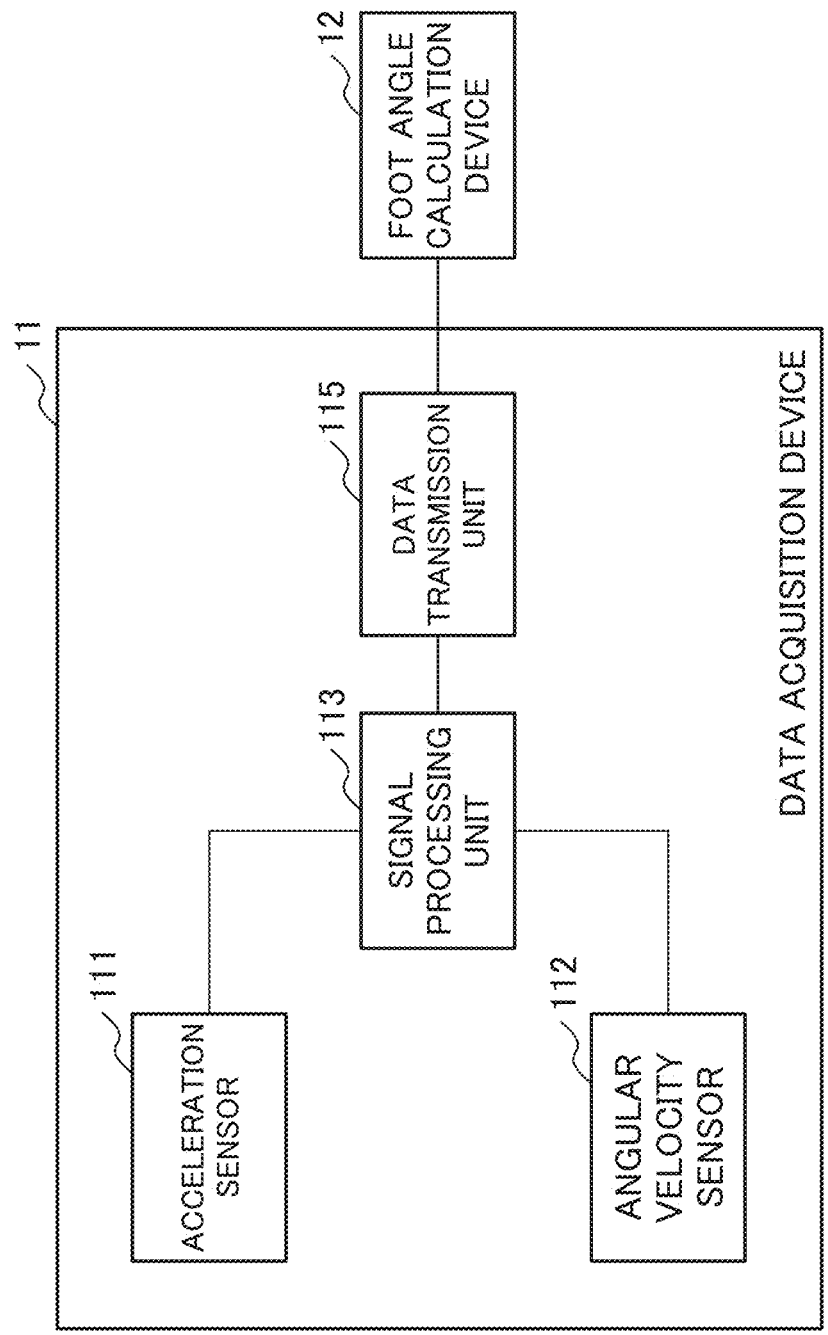
FIG. 8 is a block diagram illustrating an example of a configuration of the data acquisition device of the gait measurement system according to the first example embodiment of the present invention.

Next, details of the data acquisition device 11 included in the gait measurement system 1 will be described with reference to the drawings. FIG. 8 is a block diagram illustrating an example of a configuration of the data acquisition device 11. The data acquisition device 11 includes an acceleration sensor 111, an angular velocity sensor 112, a signal processing unit 113, and a data transmission unit 115.

The acceleration sensor 111 is a sensor that measures an acceleration in triaxial directions. The acceleration sensor 111 is connected to the signal processing unit 113. The acceleration sensor 111 outputs the measured acceleration to the signal processing unit 113.

The angular velocity sensor 112 is a sensor that measures an angular velocity in the triaxial directions. The angular velocity sensor 112 is connected to the signal processing unit 113. The angular velocity sensor 112 outputs the measured angular velocity to the signal processing unit 113.

The signal processing unit 113 is connected to the acceleration sensor 111, the angular velocity sensor 112, and the data transmission unit 115. The signal processing unit 113 acquires the acceleration and the angular velocity from the acceleration sensor 111 and the angular velocity sensor 112, respectively. The signal processing unit 113 converts the acquired acceleration and angular velocity into digital data, and outputs the converted digital data (also referred to as sensor data) to the data transmission unit 115. The sensor data includes at least acceleration data (including an acceleration vector in the triaxial directions) obtained by converting the acceleration of analog data into the digital data and angular velocity data (including an angular velocity vector in the triaxial directions) obtained by converting the angular velocity of analog data into the digital data. The acceleration data and the angular velocity data are associated with the acquisition times of the acceleration data and the angular velocity data. The signal processing unit 113 may be configured to output sensor data obtained by adding correction such as a mounting error, temperature correction, and linearity correction to the acquired acceleration data and angular velocity data.

The data transmission unit 115 is connected to the signal processing unit 113. The data transmission unit 115 is connected to the foot angle calculation device 12. The data transmission unit 115 acquires the sensor data from the signal processing unit 113. The data transmission unit 115 transmits the acquired sensor data to foot angle calculation device 12. The data transmission unit 115 may transmit the sensor data to the foot angle calculation device 12 via a wire such as a cable, or may transmit the sensor data to the foot angle calculation device 12 via wireless communication. For example, the data transmission unit 115 can be configured to transmit the sensor data to the foot angle calculation device 12 via a wireless communication function (not illustrated) conforming to a standard such as Bluetooth (registered trademark) or WiFi (registered trademark). The communication function of the data transmission unit 115 may conform to a standard other than Bluetooth (registered trademark) or WiFi (registered trademark).

The configuration of the data acquisition device 11 has been described in detail above. The configuration of FIG. 8 is an example, and the configuration of the data acquisition device 11 included in the gait measurement system 1 of the present example embodiment is not limited to the form of FIG. 8.

Foot Angle Calculation Device

Figure 9:
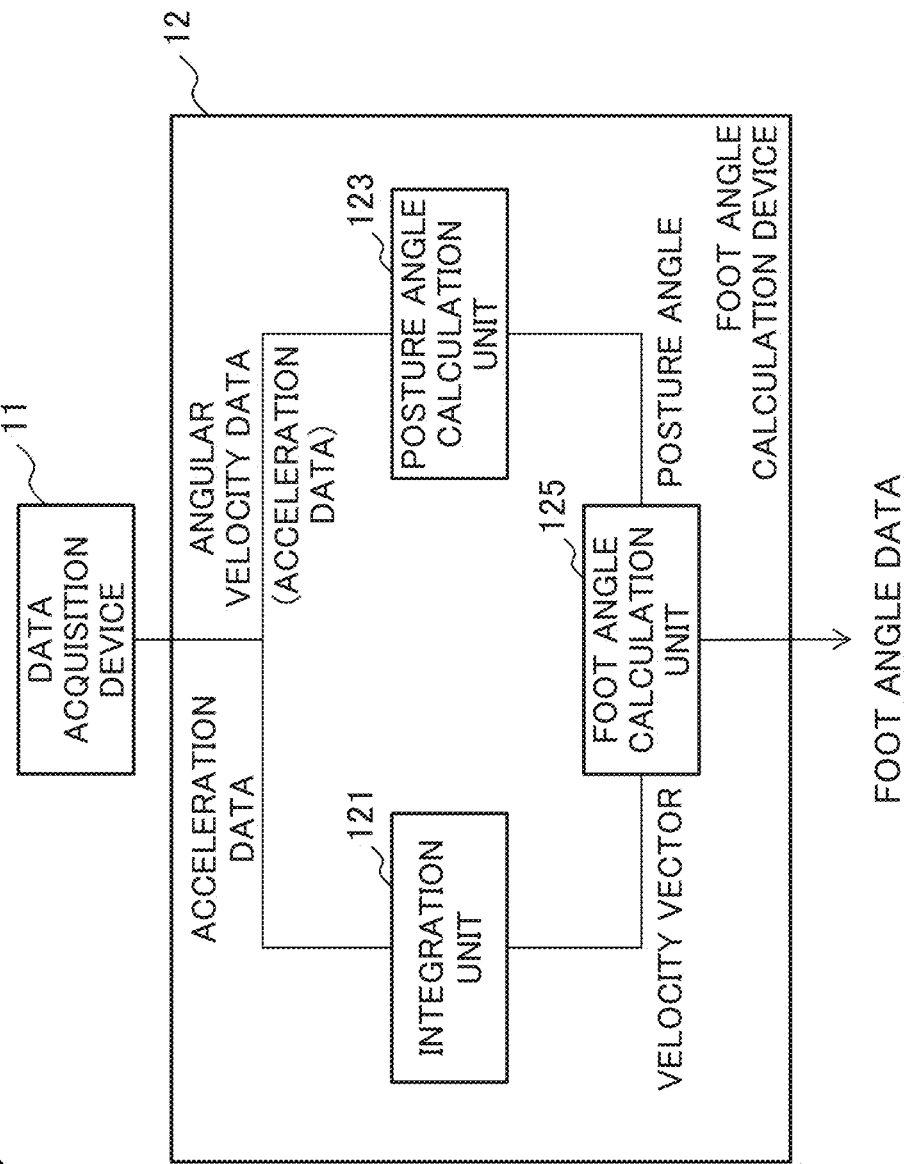
FIG. 9 is a block diagram illustrating an example of a configuration of a foot angle calculation device of the gait measurement system according to the first example embodiment of the present invention.

Next, details of the foot angle calculation device 12 included in the gait measurement system 1 will be described with reference to the drawings. FIG. 9 is a block diagram illustrating an example of a configuration of the foot angle calculation device 12. The foot angle calculation device 12 includes an integration unit 121, a posture angle calculation unit 123, and a foot angle calculation unit 125.

The integration unit 121 is connected to the data acquisition device 11. The integration unit 121 is connected to the foot angle calculation unit 125. The integration unit 121 acquires acceleration data from the data acquisition device 11. The integration unit 121 calculates a velocity vector by time-integrating the acceleration vector included in the acquired acceleration data. The integration unit 121 outputs the calculated velocity vector to the foot angle calculation unit 125.

For example, the integration unit 121 calculates a velocity vector $V(t_n)$ at a sampling time $t_n$ by using following Equation 3 (i and n are integers).

$$V(t_n) = \sum_{i=0}^{n} \frac{a(t_i)}{f_s} \quad (3)$$

In Equation 3, $a(t_i)=[a_x(t_i), a_y(t_i), a_z(t_i)]$ is an acceleration vector. Each of the vector elements $a_x(t_i)$, $a_y(t_i)$, and $a_z(t_i)$ of the acceleration vector $a(t_i)$ indicates each of an X component, a Y component, and a Z component of the acceleration vector $a(t_i)$ at the sampling time $t_i$. In Equation 3, $f_s$ is a sampling frequency. For example, the sampling frequency $f_s$ is set to 250 hertz or the like.

The posture angle calculation unit 123 is connected to the data acquisition device 11. The posture angle calculation unit 123 is connected to the foot angle calculation unit 125. The posture angle calculation unit 123 acquires angular velocity data from the data acquisition device 11. In the case of using the method of NPL 1, the posture angle calculation unit 123 acquires acceleration data in addition to the angular velocity data from the data acquisition device 11. The posture angle calculation unit 123 calculates a posture angle by using the acquired data. For example, by integrating the values of the angular velocity having each of the X axis, the Y axis, and the Z axis as a central axis, the posture angle calculation unit 123 calculates the posture angle around the axes. For example, the posture angle is represented by a roll angle $\theta_{roll}$, a pitch angle $\theta_{pitch}$, and a yaw angle $\theta_{yaw}$. The roll angle $\theta_{roll}$, the pitch angle $\theta_{pitch}$, and the yaw angle $\theta_{yaw}$ represent rotation about the Y, X, and Z axes as central axes, respectively. The posture angle calculation unit 123 outputs the calculated posture angle to the foot angle calculation unit 125.

The foot angle calculation unit 125 is connected to the integration unit 121 and the posture angle calculation unit 123. The foot angle calculation unit 125 is connected to an external system or device (not illustrated). The foot angle calculation unit 125 acquires the velocity vector from the integration unit 121 and acquires the posture angle from the posture angle calculation unit 123. The foot angle calculation unit 125 calculates a foot angle by using the velocity vector and the posture angle. For example, the foot angle calculation unit 125 calculates the velocity angle $\theta_v$, which is an angle formed by the velocity vector V and the Y axis on the floor plane, by using Equation 1 described above. Then, the foot angle calculation unit 125 calculates the foot angle $\theta$ by using Equation 2 described above. When acquiring the velocity angle $\theta_v$ of each of the left foot and the right foot, the foot angle calculation unit 125 can separately calculate the foot angle $\theta_L$ of the left foot and the foot angle $\theta_R$ of the right foot. The foot angle calculation unit 125 outputs the calculated foot angle to the external system or device (not illustrated).

The configuration of the foot angle calculation device 12 has been described in detail above. The configuration of FIG. 9 is an example, and the configuration of the foot angle calculation device 12 included in the gait measurement system 1 of the present example embodiment is not limited to the form of FIG. 9.

Gait Cycle

Figure 10:
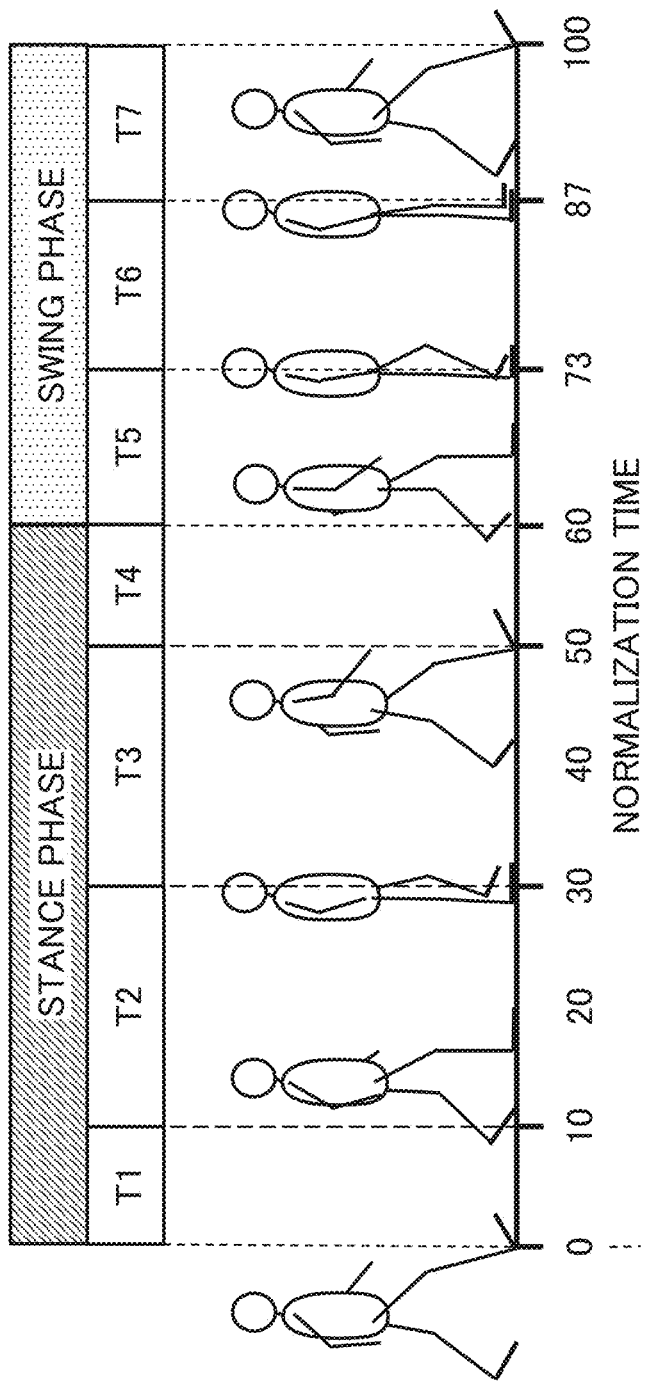
FIG. 10 is a conceptual diagram for describing a change in a gait cycle of a general pedestrian.

Here, a period suitable for calculating the velocity vector by the gait measurement system 1 will be described with reference to the drawings. FIG. 10 is a conceptual diagram for describing the gait cycle of a general pedestrian. The horizontal axis in FIG. 10 represents time normalized with one gait cycle of one foot as 100% (also referred to as normalization time).

In general, one gait cycle of one foot is roughly divided into a stance phase in which at least a part of the back side of the foot is in contact with the ground and a swing phase in which the back side of the foot is away from the ground. The stance phase is further classified into a loading response period T1, a mid-stance period T2, a terminal stance period T3, and a pre-swing period T4. The swing phase is further classified into an initial swing period T5, a mid-swing period T6, and a terminal swing period T7.

Figure 11:
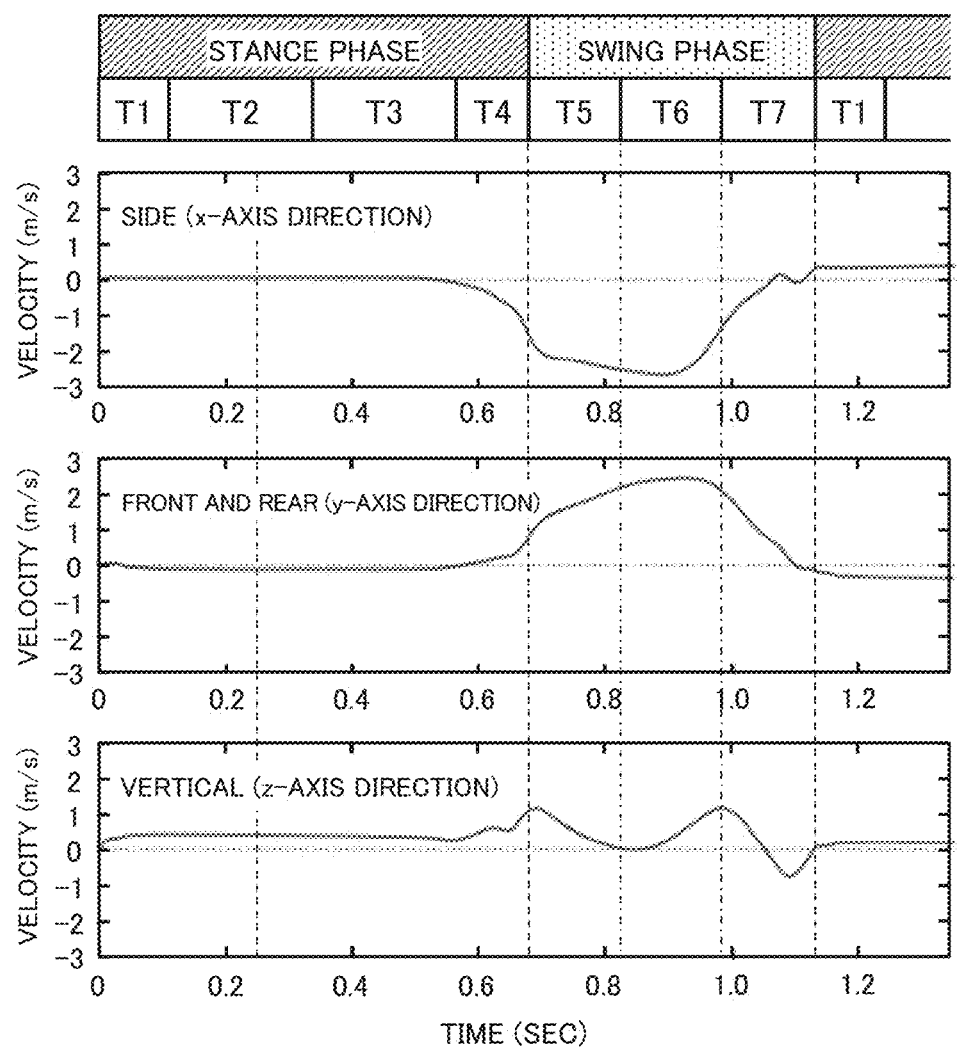
FIG. 11 is a graph illustrating an example of time-series data of a velocity vector calculated by the gait measurement system according to the first example embodiment of the present invention.

FIG. 11 is an example of time-series data of velocities in the X-axis, Y-axis, and Z-axis directions. The velocity in the Y-axis direction in the swing phase is relatively less changed in the mid-swing period T6 than in the initial swing period T5 and the terminal swing period T7. Therefore, the foot angle can be accurately calculated by using the velocity vector calculated in the mid-swing period T6 in which a velocity change is relatively small. For example, the foot angle calculation device 12 calculates the foot angle by using the velocity vector averaged in the swing phase. For example, the foot angle calculation device 12 calculates the foot angle by using the velocity vector weighted for the mid-swing period included in the swing phase.

The configuration of the gait measurement system 1 of the present example embodiment has been described above. The configurations of FIGS. 1, 8, and 9 are examples, and the configuration of the gait measurement system 1 of the present example embodiment is not limited to the configurations of FIGS. 1, 8, and 9.

Operation

Figure 12:
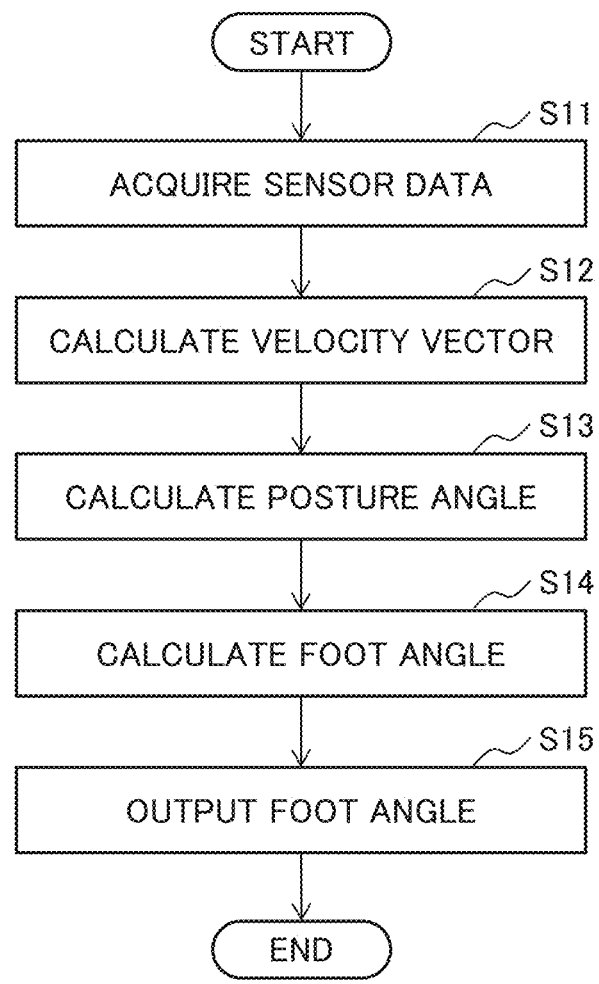
FIG. 12 is a flowchart for describing an example of an operation of the foot angle calculation device of the gait measurement system according to the first example embodiment of the present invention.

Next, an example of the operation of the foot angle calculation device 12 of the present example embodiment will be described with reference to the drawings. FIG. 12 is a flowchart for describing the example of the operation of the foot angle calculation device 12. In the following description along the flowchart of FIG. 12, the foot angle calculation device 12 is a main operation body.

In FIG. 12, first, the foot angle calculation device 12 acquires the sensor data from the data acquisition device 11 (step S11).

Next, the foot angle calculation device 12 calculates a velocity vector by time-integrating the acceleration vector included in the sensor data (step S12).

Next, the foot angle calculation device 12 calculates a posture angle by using the angular velocity data included in the sensor data (step S13). The order of the calculation of the velocity vector (step S12) and the calculation of the posture angle (step S13) may be changed, or may be performed in parallel.

Next, the foot angle calculation device 12 calculates a foot angle by using the velocity vector and the posture angle (step S14).

Then, the foot angle calculation device 12 outputs the calculated foot angle (step S15).

The example of the operation of the foot angle calculation device 12 of the present example embodiment has been described above. The flowchart of FIG. 12 is an example, and the operation of the foot angle calculation device 12 of the present example embodiment is not limited to the processing along the flowchart of FIG. 12.

As described above, the foot angle calculation device of the present example embodiment includes the integration unit, the posture angle calculation unit, and the foot angle calculation unit. The integration unit calculates a velocity vector by time-integrating the acceleration vector. The posture angle calculation unit calculates a posture angle by using the angular velocity vector of the foot portion. The foot angle calculation unit calculates a foot angle, which is an angle formed by the velocity vector and the center line of the foot, by using the velocity vector and the posture angle of the foot portion.

In one aspect of the present example embodiment, the foot angle calculation unit calculates the foot angle by using the velocity vector averaged in the swing phase. In one aspect of the present example embodiment, the foot angle calculation unit calculates the foot angle by using the velocity vector weighted in the mid-swing period included in the swing phase. In one aspect of the present example embodiment, the foot angle calculation unit calculates the foot angle by using the velocity vector in the mid-swing period included in the swing phase.

The gait measurement system according to one aspect of the present example embodiment includes the data acquisition device that measures acceleration and angular velocity of the foot portion and generates the sensor data including the acceleration vector and the angular velocity vector by using the measured acceleration and angular velocity. The data acquisition device transmits the generated sensor data to the foot angle calculation device.

According to the present example embodiment, the velocity vector is used to accurately follow the traveling direction that changes with the direction of the pedestrian, and thus the foot angle of the pedestrian can be easily measured with high accuracy.

Second Example Embodiment

Next, a gait measurement system according to a second example embodiment of the present invention will be described with reference to the drawings. The gait measurement system of the present example embodiment is different from the gait measurement system of the first example embodiment in that the velocity vector is calculated on the data acquisition device side. Hereinafter, the description of the same configuration and operation as those of the first example embodiment may be omitted.

Configuration

Figure 13:
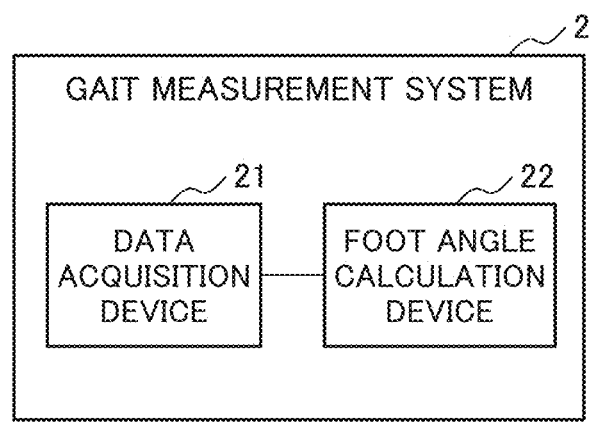
FIG. 13 is a block diagram illustrating an example of a configuration of a gait measurement system according to a second example embodiment of the present invention.

FIG. 13 is a block diagram illustrating an outline of a configuration of a gait measurement system 2 of the present example embodiment. The gait measurement system 2 includes a data acquisition device 21 and a foot angle calculation device 22. The data acquisition device 21 and the foot angle calculation device 22 may be connected by wire or may be connected wirelessly. The data acquisition device 21 and the foot angle calculation device 22 may be configured by a single device. The data acquisition device 21 may be removed from the configuration of the gait measurement system 2, and the gait measurement system 2 may be configured only by the foot angle calculation device 22.

The data acquisition device 21 is connected to the foot angle calculation device 22. The data acquisition device 21 includes at least an acceleration sensor and an angular velocity sensor. The data acquisition device 21 converts the data acquired by the acceleration sensor and the angular velocity sensor into digital data. The data acquisition device 21 calculates a velocity vector by using the data acquired by the acceleration sensor. The data acquisition device 21 calculates the velocity vector by using an acceleration vector by a method similar to that of the integration unit 121 of the foot angle calculation device 12 included in the gait measurement system 1 of the first example embodiment. The data acquisition device 21 transmits, to the foot angle calculation device 22, sensor data including the acceleration vector, the angular velocity vector, and the velocity vector converted into the digital data. The data acquisition device 21 has a configuration corresponding to the data acquisition device 11 of the first example embodiment.

The foot angle calculation device 22 is connected to the data acquisition device 21. The foot angle calculation device 22 receives the sensor data from the data acquisition device 21. The foot angle calculation device 22 calculates a foot angle by using the received sensor data. More specifically, the foot angle calculation device 22 calculates a posture angle by using the angular velocity data, and calculates the foot angle by using the velocity vector and the posture angle.

The foot angle calculation device 22 has a configuration corresponding to the foot angle calculation device 12 of the first example embodiment.

The outline of the configuration of the gait measurement system 2 of the present example embodiment has been described above. The configuration of FIG. 13 is an example, and the gait measurement system 2 of the present example embodiment is not limited to the configuration of FIG. 13.

Data Acquisition Device

Figure 14:
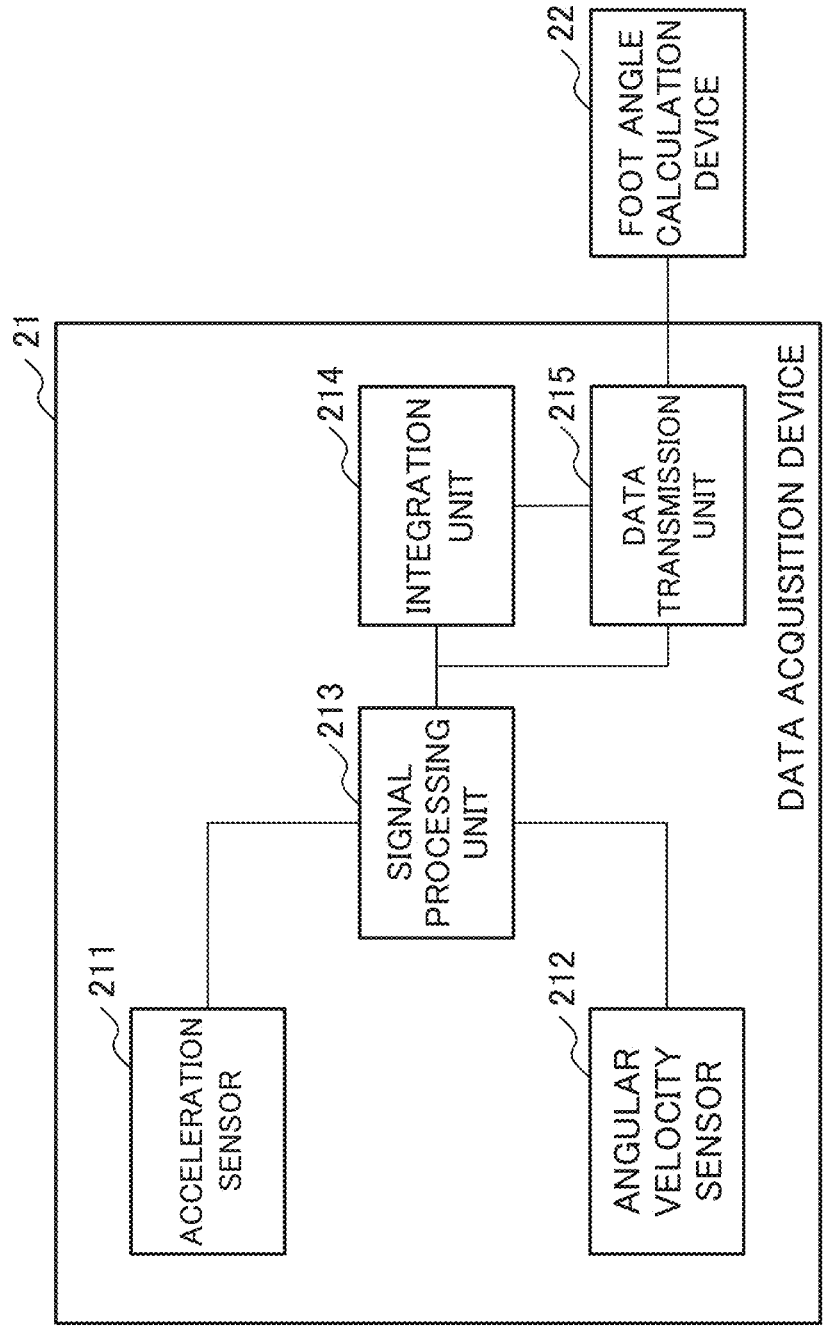
FIG. 14 is a block diagram illustrating an example of a configuration of a data acquisition device of the gait measurement system according to the second example embodiment of the present invention.

Next, details of the data acquisition device 21 included in the gait measurement system 2 will be described with reference to the drawings. FIG. 14 is a block diagram illustrating an example of a configuration of the data acquisition device 21. The data acquisition device 21 includes an acceleration sensor 211, an angular velocity sensor 212, a signal processing unit 213, an integration unit 214, and a data transmission unit 215.

The acceleration sensor 211 is a sensor that measures an acceleration in the triaxial directions. The acceleration sensor 211 is connected to the signal processing unit 213. The acceleration sensor 211 outputs the measured acceleration to the signal processing unit 213. The acceleration sensor 211 has a configuration corresponding to the acceleration sensor 111 of the first example embodiment.

The angular velocity sensor 212 is a sensor that measures an angular velocity in the triaxial directions. The angular velocity sensor 212 is connected to the signal processing unit 213. The angular velocity sensor 212 outputs the measured angular velocity to the signal processing unit 213. The angular velocity sensor 212 has a configuration corresponding to the angular velocity sensor 112 of the first example embodiment.

The signal processing unit 213 is connected to the acceleration sensor 211, the angular velocity sensor 212, the integration unit 214, and the data transmission unit 215. The signal processing unit 213 acquires the acceleration and the angular velocity from the acceleration sensor 211 and the angular velocity sensor 212, respectively. The signal processing unit 213 converts the acquired acceleration and angular velocity into digital data. The signal processing unit 213 outputs the converted acceleration data to the integration unit 214. The signal processing unit 213 outputs the converted acceleration data (including the acceleration vector in the triaxial directions) and the angular velocity data (including the angular velocity vector in the triaxial directions) to the data transmission unit 215. The signal processing unit 213 has a configuration corresponding to the signal processing unit 113 of the first example embodiment.

The integration unit 214 is connected to the signal processing unit 213 and the data transmission unit 215. The integration unit 214 acquires the acceleration vector from the signal processing unit 213. The integration unit 214 calculates a velocity vector by time-integrating the acquired acceleration vector. The integration unit 214 calculates the velocity vector by a method similar to that of the integration unit 121 of the first example embodiment. The integration unit 214 outputs the calculated velocity vector to the data transmission unit 215. The integration unit 214 has a configuration corresponding to the integration unit 121 of the first example embodiment.

The data transmission unit 215 is connected to the signal processing unit 213 and the integration unit 214. The data transmission unit 215 is connected to the foot angle calculation device 22. The data transmission unit 215 acquires the acceleration vector and the angular velocity vector from the signal processing unit 213. The data transmission unit 215 also acquires the velocity vector from the integration unit 214. The data transmission unit 215 transmits, to the foot angle calculation device 22, sensor data including the acceleration vector, the angular velocity vector, and the velocity vector based on the acceleration and the angular velocity measured at the same timing. The data transmission unit 215 has a configuration corresponding to the data transmission unit 115 of the first example embodiment.

The configuration of the data acquisition device 21 has been described in detail above. The configuration of FIG. 14 is an example, and the configuration of the data acquisition device 21 included in the gait measurement system 2 of the present example embodiment is not limited to the form of FIG. 14.

Foot Angle Calculation Device

Figure 15:
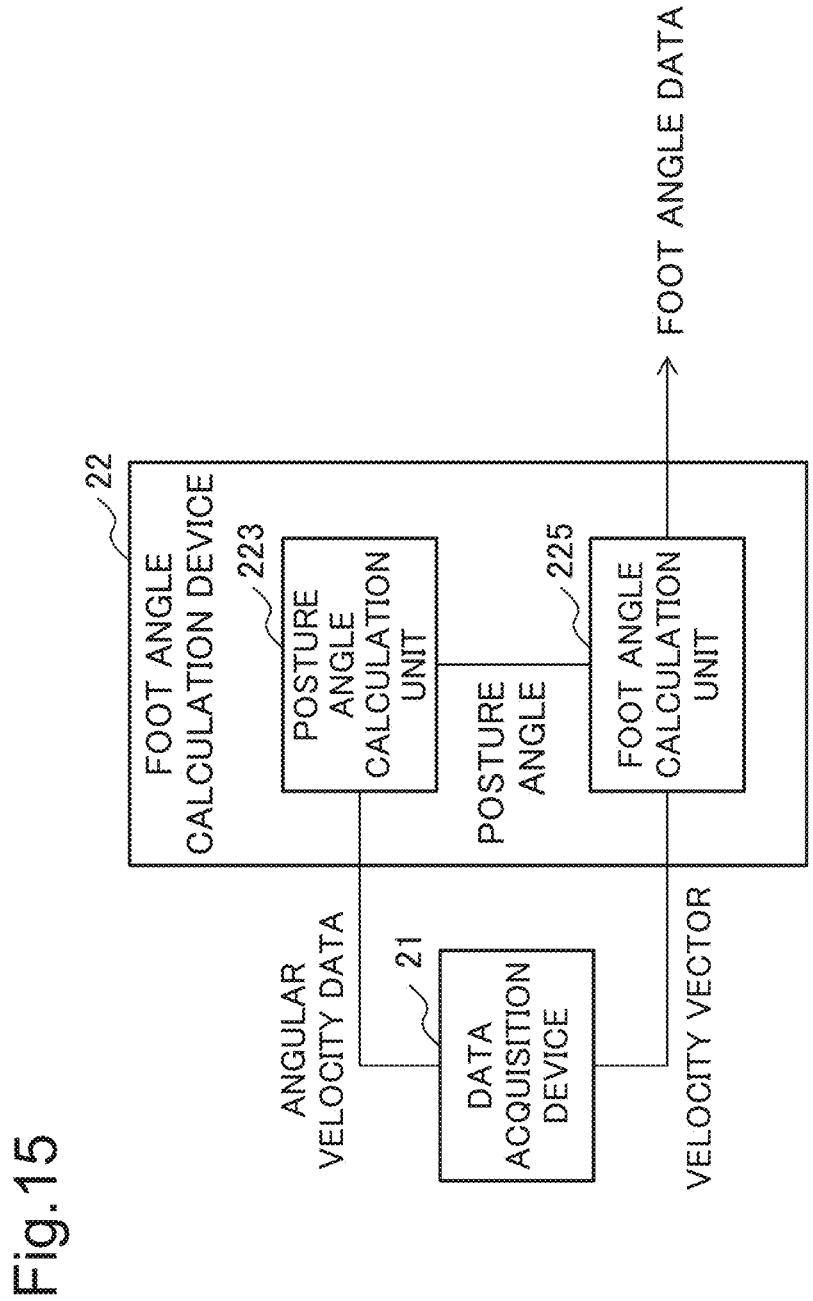
FIG. 15 is a block diagram for describing an example of a configuration of a foot angle calculation device of the gait measurement system according to the second example embodiment of the present invention.

Next, details of the foot angle calculation device 22 included in the gait measurement system 2 will be described with reference to the drawings. FIG. 15 is a block diagram illustrating an example of a configuration of the foot angle calculation device 22. The foot angle calculation device 22 includes a posture angle calculation unit 223 and a foot angle calculation unit 225.

The posture angle calculation unit 223 is connected to the data acquisition device 21. The posture angle calculation unit 223 is connected to the foot angle calculation unit 225. The posture angle calculation unit 223 acquires angular velocity data from the data acquisition device 21. In the case of using the method of NPL 1, the posture angle calculation unit 223 acquires acceleration data in addition to the angular velocity data from the data acquisition device 21. The posture angle calculation unit 223 calculates a posture angle by using the acquired data. The posture angle calculation unit 223 outputs the calculated posture angle to the foot angle calculation unit 225. The posture angle calculation unit 223 has a configuration corresponding to the posture angle calculation unit 123 of the first example embodiment.

The foot angle calculation unit 225 is connected to the posture angle calculation unit 223. The foot angle calculation unit 225 is connected to the external system or device (not illustrated). The foot angle calculation unit 225 acquires the velocity vector from the data acquisition device 21 and acquires the posture angle from the posture angle calculation unit 223. The foot angle calculation unit 225 calculates a foot angle by using the velocity vector and the posture angle. The foot angle calculation unit 225 outputs the calculated foot angle to the external system or device (not illustrated). The foot angle calculation unit 225 has a configuration corresponding to the foot angle calculation unit 125 of the first example embodiment.

The configuration of the foot angle calculation device 22 has been described in detail above. The configuration of FIG. 15 is an example, and the configuration of the foot angle calculation device 22 included in the gait measurement system 2 of the present example embodiment is not limited to the form of FIG. 15.

Operation

Figure 16:
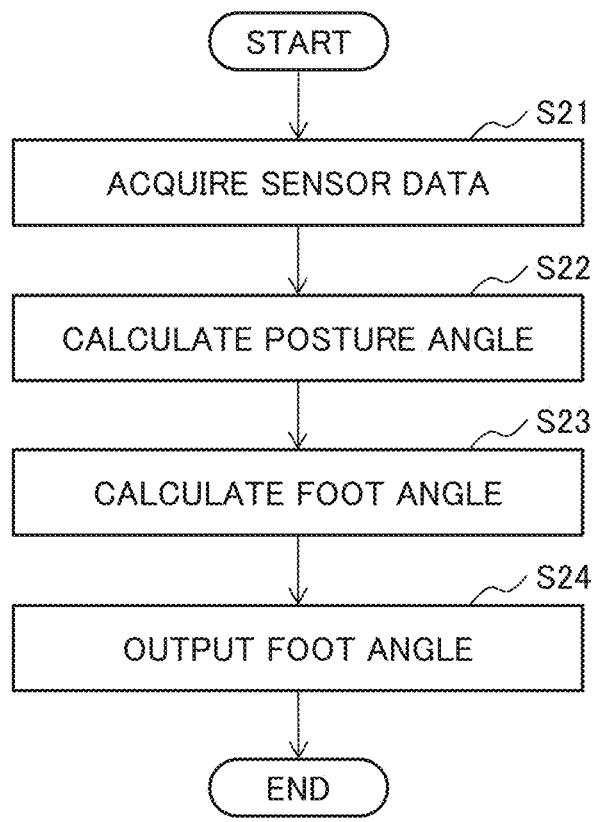
FIG. 16 is a flowchart for describing an example of an operation of the foot angle calculation device of the gait measurement system according to the second example embodiment of the present invention.

Next, an example of the operation of the foot angle calculation device 22 of the present example embodiment will be described with reference to the drawings. FIG. 16 is a flowchart for describing an example of the operation of the foot angle calculation device 22. In the following description along the flowchart of FIG. 16, the foot angle calculation device 22 is a main operation body.

In FIG. 16, first, the foot angle calculation device 22 acquires the sensor data from the data acquisition device 21 (step S21).

Next, the foot angle calculation device 22 calculates a posture angle by using the angular velocity data included in the sensor data (step S22).

Next, the foot angle calculation device 22 calculates a foot angle by using the velocity data and the posture angle (step S23).

Then, the foot angle calculation device 22 outputs the calculated foot angle (step S24).

The example of the operation of the foot angle calculation device 22 of the present example embodiment has been described above. The flowchart of FIG. 16 is an example, and the operation of the foot angle calculation device 22 of the present example embodiment is not limited to the processing along the flowchart of FIG. 16.

As described above, the foot angle calculation device according to the present example embodiment includes the posture angle calculation unit that calculates the posture angle by using the angular velocity data of the foot portion, and the foot angle calculation unit that calculates the foot angle, which is the angle formed by the velocity vector and the center line of the foot, by using the velocity vector and the posture angle of the foot portion.

In one aspect of the present example embodiment, the data acquisition device calculates the velocity vector by using the measured acceleration. The foot angle calculation unit calculates the foot angle by using the velocity vector calculated by the data acquisition device and the posture angle.

According to the present example embodiment, the velocity vector is used to accurately follow the traveling direction that changes with the direction of the pedestrian, and thus the foot angle of the pedestrian can be easily measured with high accuracy.

Third Example Embodiment

Next, a gait measurement system according to a third example embodiment of the present invention will be described with reference to the drawings. The gait measurement system of the present example embodiment is different from the gait measurement systems of the first and second example embodiments in that a display device that displays information regarding the foot angle of the pedestrian is provided. Hereinafter, a configuration in which the display device is added to the gait measurement system of the first example embodiment will be exemplified, and description of the same configuration and operation as those of the first example embodiment may be omitted.

Configuration

Figure 17:
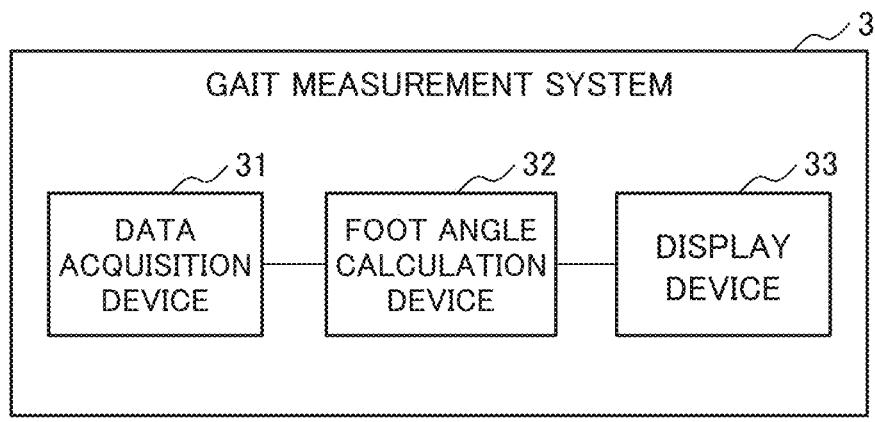
FIG. 17 is a block diagram illustrating an example of a configuration of a gait measurement system according to a third example embodiment of the present invention.

FIG. 17 is a block diagram illustrating an outline of a configuration of a gait measurement system 3 of the present example embodiment. The gait measurement system 3 includes a data acquisition device 31, a foot angle calculation device 32, and a display device 33. The data acquisition device 31, the foot angle calculation device 32, and the display device 33 may be connected by wire or may be connected wirelessly. The data acquisition device 31, the foot angle calculation device 32, and the display device 33 may be configured by a single device.

The data acquisition device 31 is connected to the foot angle calculation device 32. The data acquisition device 31 includes at least an acceleration sensor and an angular velocity sensor. The data acquisition device 31 converts the data acquired by the acceleration sensor and the angular velocity sensor into digital data (also referred to as sensor data), and transmits the converted sensor data to the foot angle calculation device 32. The data acquisition device 31 has a configuration corresponding to the data acquisition device 11 of the first example embodiment.

The foot angle calculation device 32 is connected to the data acquisition device 31 and the display device 33. Similarly to the foot angle calculation device 12 of the first example embodiment, the foot angle calculation device 32 includes an integration unit, a posture angle calculation unit, and a foot angle calculation unit (not illustrated). The foot angle calculation device 32 receives the sensor data from the data acquisition device 31. The foot angle calculation device 32 calculates a foot angle by using the received sensor data. More specifically, the integration unit of the foot angle calculation device 32 calculates a velocity vector by time-integrating the acceleration vector of the foot portion. The posture angle calculation unit of the foot angle calculation device 32 calculates a posture angle by using the angular velocity data. The foot angle calculation unit of the foot angle calculation device 32 calculates a foot angle by using the velocity vector and the posture angle. The foot angle calculation unit of the foot angle calculation device 32 outputs information regarding the calculated foot angle to the display device 33. For example, the foot angle calculation device 32 may output the ratio of the durations of the stance phase and the swing phase, a stride length, a walking speed, the height of the sensor, and the like. The foot angle calculation device 32 has a configuration corresponding to the foot angle calculation device 12 of the first example embodiment. The integration unit may be included in the data acquisition device 31. In a case where the integration unit is included in the data acquisition device 31, the foot angle calculation device 32 corresponds to the foot angle calculation device 22 of the second example embodiment.

The display device 33 is connected to the foot angle calculation device 32. The display device 33 acquires the information regarding the foot angle from the foot angle calculation device 32. The display device 33 displays the acquired information regarding the foot angle on a monitor of the display device 33.

Figure 18:
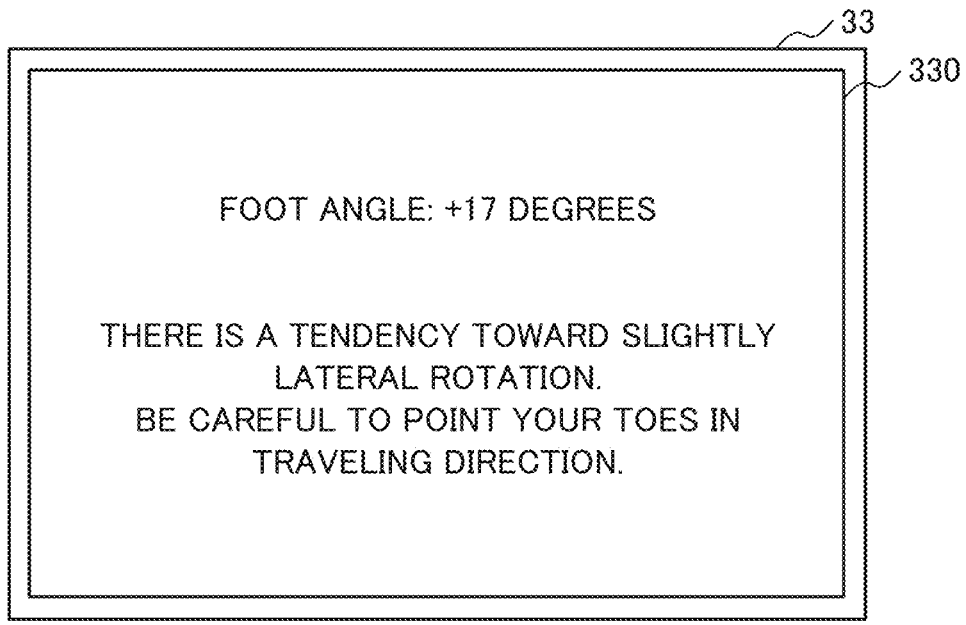
FIG. 18 is a conceptual diagram illustrating an example of information to be displayed on a monitor of a display device of the gait measurement system according to the third example embodiment of the present invention.

FIG. 18 illustrates an example in which the foot angle of the pedestrian and the information regarding the foot angle are displayed on a monitor 330 of the display device 33. In the example of FIG. 18, in a case where the foot angle is equal to or more than +15 degrees, it is determined that "there is a tendency toward slightly lateral rotation". FIG. 18 illustrates an example in which the foot angle (+17 degrees) calculated by the foot angle calculation device 32 and the comment relevant to the foot angle (+17 degrees) are displayed on the monitor 330. For example, the monitor 330 displays, as the comment relevant to the foot angle, information indicating whether the foot angle has tendency toward lateral rotation or medial rotation, and information indicating an advice on the walking relevant to the foot angle.

Figure 19:
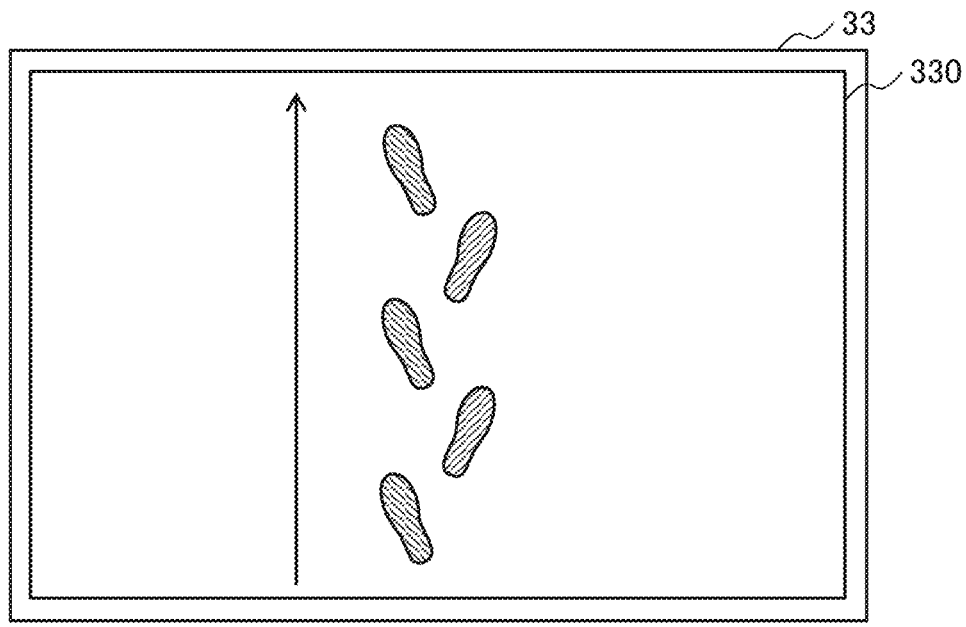
FIG. 19 is a conceptual diagram illustrating another example of the information to be displayed on the monitor of the display device of the gait measurement system according to the third example embodiment of the present invention.

FIG. 19 illustrates an example in which the foot type relevant to the foot angle of the pedestrian is displayed on the monitor 330 of the display device 33. In the example of FIG. 19, the foot type is displayed on the monitor 330 in time series in accordance with the foot angle of the pedestrian for each step.

The user who visually recognizes the information displayed on the monitor 330 of the display device 33 as in the examples of FIGS. 18 and 19 can estimate the walking state of the pedestrian according to the information displayed on the monitor 330. For example, in a case where the user of the gait measurement system 3 checks the walking state of the pedestrian, the information is displayed on the monitor 330 that can be visually recognized by the user. For example, in a case where the user of the gait measurement system 3 is the pedestrian himself/herself, the information is displayed on the monitor 330 that can be visually recognized by the pedestrian. The information displayed on the monitor 330 is not limited to the examples of FIGS. 18 and 19 as long as the information is relevant to the foot angle.

The outline of the configuration of the gait measurement system 3 of the present example embodiment has been described above. The configuration of FIG. 17 is an example, and the gait measurement system 3 of the present example embodiment is not limited to the configuration of FIG. 17.

Operation

Figure 20:
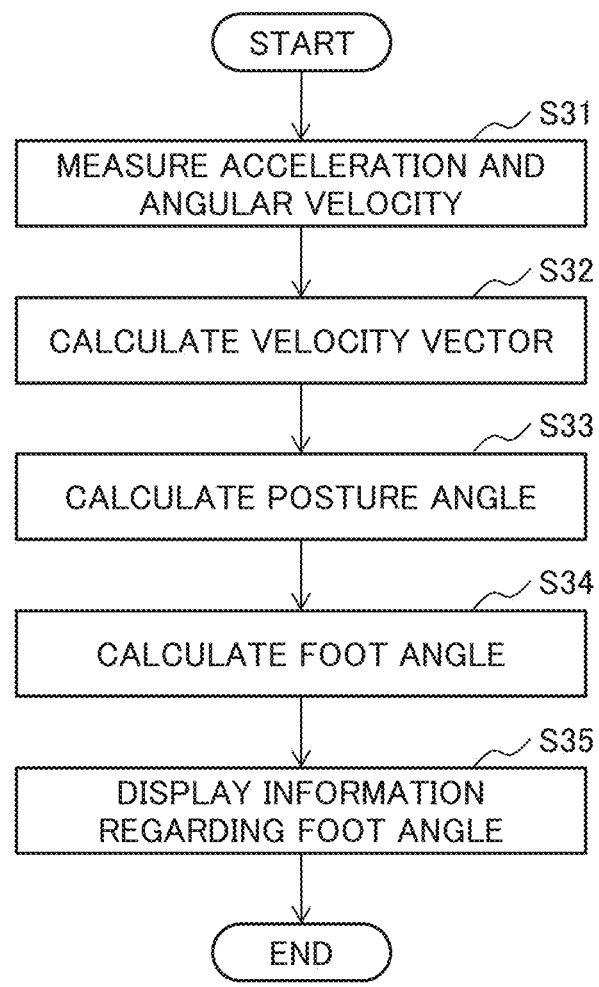
FIG. 20 is a flowchart for describing an example of an operation of the gait measurement system according to the third example embodiment of the present invention.

Next, an example of an operation of the gait measurement system 3 of the present example embodiment will be described with reference to the drawings. FIG. 20 is a flowchart for describing an example of the operation of the gait measurement system 3. In the following description along the flowchart of FIG. 20, the gait measurement system 3 is a main operation body.

In FIG. 20, first, the gait measurement system 3 measures an acceleration and an angular velocity (step S31).

Next, the gait measurement system 3 calculates a velocity vector by time-integrating the acceleration vector (step S32).

Next, the gait measurement system 3 calculates a posture angle by using the angular velocity data (step S33). The order of the calculation of the velocity vector (step S32) and the calculation of the posture angle (step S33) may be changed, or may be performed in parallel.

Next, the gait measurement system 3 calculates a foot angle by using the velocity vector and the posture angle (step S34).

Then, the gait measurement system 3 displays information regarding the calculated foot angle (step S35).

An example of the operation of the gait measurement system 3 of the present example embodiment has been described above. The flowchart of FIG. 20 is an example, and the operation of the gait measurement system 3 of the present example embodiment is not limited to the processing along the flowchart of FIG. 20.

As described above, the foot angle calculation unit of the foot angle calculation device included in the gait measurement system of the present example embodiment outputs the information regarding the calculated foot angle to the display device. The information regarding the foot angle output from the foot angle calculation unit is displayed on the display device. According to the present example embodiment, the walking state of the pedestrian can be estimated by referring to the information regarding the foot angle displayed on the display device.

Fourth Example Embodiment

Next, a gait measurement system according to a fourth example embodiment of the present invention will be described with reference to the drawings. The gait measurement system of the present example embodiment is different from the gait measurement systems of the first to third example embodiments in that a notification device that performs notification according to the foot angle of the pedestrian is provided. Hereinafter, a configuration in which the notification device is added to the gait measurement system of the first example embodiment will be exemplified, and description of the same configuration and operation as those of the first example embodiment may be omitted.

Configuration

Figure 21:
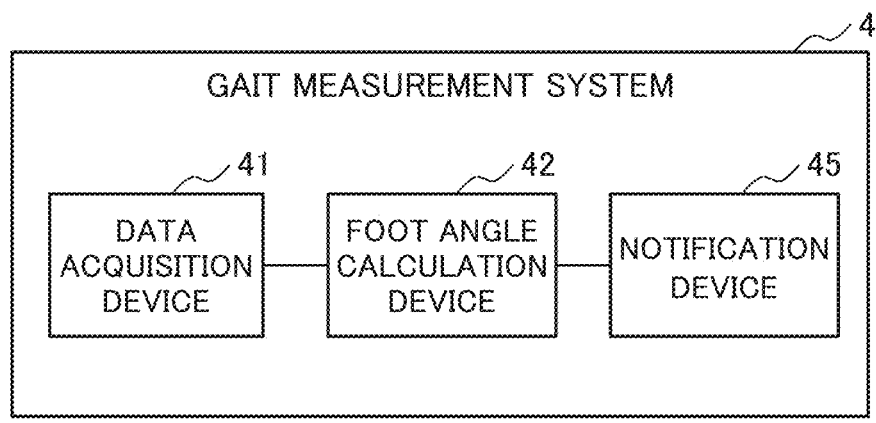
FIG. 21 is a block diagram illustrating an example of a configuration of a gait measurement system according to a fourth example embodiment of the present invention.

FIG. 21 is a block diagram illustrating an outline of a configuration of a gait measurement system 4 of the present example embodiment. The gait measurement system 4 includes a data acquisition device 41, a foot angle calculation device 42, and a notification device 45. The data acquisition device 41, the foot angle calculation device 42, and the notification device 45 may be connected by wire or may be connected wirelessly. The data acquisition device 41, the foot angle calculation device 42, and the notification device 45 may be configured by a single device.

The data acquisition device 41 is connected to the foot angle calculation device 42. The data acquisition device 41 includes at least an acceleration sensor and an angular velocity sensor. The data acquisition device 41 converts the data acquired by the acceleration sensor into digital data (also referred to as sensor data), and transmits the converted sensor data to the foot angle calculation device 42. The data acquisition device 41 has a configuration corresponding to the data acquisition device 11 of the first example embodiment.

The foot angle calculation device 42 is connected to the data acquisition device 41 and the notification device 45. Similarly to the foot angle calculation device 12 of the first example embodiment, the foot angle calculation device 42 includes an integration unit, a posture angle calculation unit, and a foot angle calculation unit (not illustrated). The foot angle calculation device 42 receives the sensor data from the data acquisition device 41. The foot angle calculation device 42 calculates a foot angle by using the received sensor data. More specifically, the integration unit of the foot angle calculation device 42 calculates a velocity vector by time-integrating the acceleration vector. The posture angle calculation unit of the foot angle calculation device 42 calculates a posture angle by using the angular velocity data. The foot angle calculation unit of the foot angle calculation device 42 calculates a foot angle by using the velocity vector and the posture angle. The foot angle calculation unit of the foot angle calculation device 42 outputs information regarding the calculated foot angle to the notification device 45. For example, the foot angle calculation device 42 may output the ratio of the durations of the stance phase and the swing phase, the stride length, the walking speed, the height of the sensor, and the like. The foot angle calculation device 42 has a configuration corresponding to the foot angle calculation device 12 of the first example embodiment. The integration unit may be included in the data acquisition device 41. In a case where the integration unit is included in the data acquisition device 41, the foot angle calculation device 42 corresponds to the foot angle calculation device 22 of the second example embodiment.

The notification device 45 is connected to the foot angle calculation device 42. The notification device 45 acquires the information regarding the foot angle from the foot angle calculation device 42. The notification device 45 performs notification according to the acquired foot angle value. For example, the notification device 45 includes a light emitting unit, and causes the light emitting unit to emit light in a case where the foot angle value exceeds or falls below a threshold. For example, the notification device 45 includes a speaker, and emits a sound from the speaker in a case where the foot angle value exceeds or falls below the threshold. For example, the notification device 45 includes a vibration unit, and causes the vibration unit to vibrate in a case where the foot angle value exceeds or falls below the threshold. For example, in a case where notification device 45 includes the light emitting unit, the speaker, the vibration unit, and the like, the intensity of light emitted from the light emitting unit, the volume of the speaker, and the vibration of the vibration unit is increased or decreased according to the degree to which the foot angle value exceeds or falls below the threshold. For example, in a case where the notification device 45 includes the light emitting unit, the speaker, the vibration unit, and the like, and the foot angle value is within a normal range, the notification device may be configured to notify that the foot angle is normal by using the intensity of light emitted from the light emitting unit, the volume of the speaker, and the vibration of the vibration unit. A notification method by the notification device 45 is not limited to the example described herein as long as the state of the foot angle can be notified.

The user who has checked the notification by the notification device 45 can estimate the walking state of the pedestrian based on the notified information. For example, in a case where the user of the gait measurement system 4 checks the walking state of the pedestrian, the light emitting unit is caused to emit light, the speaker is caused to emit a sound, or the vibration unit is caused to vibrate in such a way that the user can check the walking state. For example, in a case where the user of the gait measurement system 4 is the pedestrian himself/herself, the light emitting unit is caused to emit the light, the speaker is caused to emit the sound, or the vibration unit is caused to vibrate in such a way that the pedestrian can check the walking state.

The outline of the configuration of the gait measurement system 4 of the present example embodiment has been described above. The configuration of FIG. 21 is an example, and the gait measurement system 4 of the present example embodiment is not limited to the configuration of FIG. 21.

Operation

Figure 22:
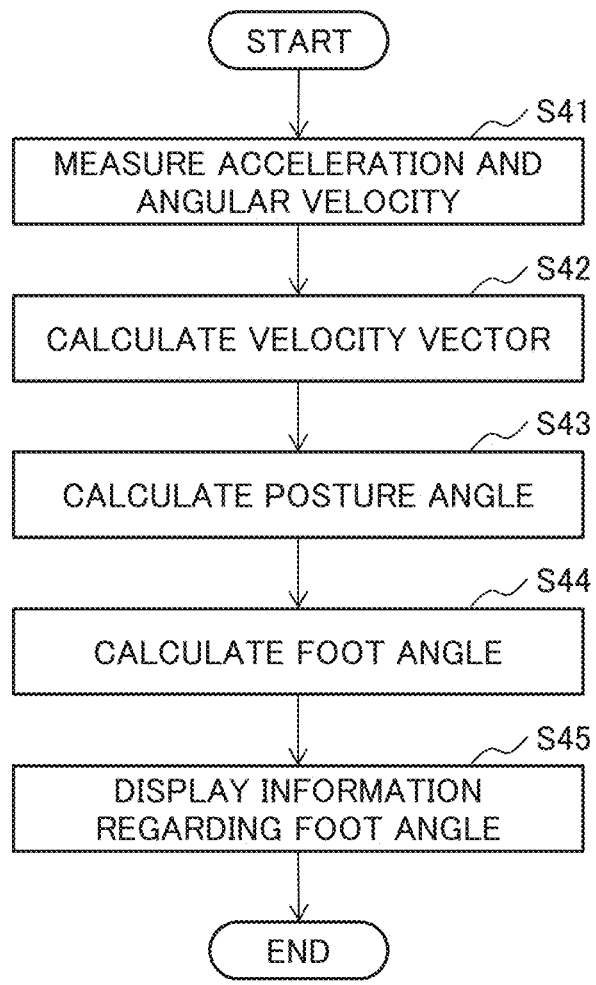
FIG. 22 is a flowchart for describing an example of an operation of the gait measurement system according to the fourth example embodiment of the present invention.

Next, an example of an operation of the gait measurement system 4 of the present example embodiment will be described with reference to the drawings. FIG. 22 is a flowchart for describing an example of the operation of the gait measurement system 4. In the following description along the flowchart of FIG. 22, the gait measurement system 4 is a main operation body.

In FIG. 22, first, the gait measurement system 4 measures an acceleration and an angular velocity (step S41).

Next, the gait measurement system 4 calculates a velocity vector by time-integrating the acceleration vector (step S42).

Next, the gait measurement system 4 calculates a posture angle by using the angular velocity data (step S43). The order of the calculation of the velocity vector (step S42) and the calculation of the posture angle (step S43) may be changed, or may be performed in parallel.

Next, the gait measurement system 4 calculates a foot angle by using the velocity vector and the posture angle (step S44).

Then, the gait measurement system 4 notifies information regarding the calculated foot angle (step S45).

An example of the operation of the gait measurement system 4 of the present example embodiment has been described above. The flowchart of FIG. 22 is an example, and the operation of the gait measurement system 4 of the present example embodiment is not limited to the processing along the flowchart of FIG. 22.

As described above, the foot angle calculation unit of the foot angle calculation device included in the gait measurement system of the present example embodiment outputs the information regarding the calculated foot angle to the notification device. The information regarding the foot angle output from the foot angle calculation unit is notified by the notification device. According to the present example embodiment, the information regarding the foot angle can be recognized based on the notification by the notification device.

Hardware

Here, a hardware configuration for achieving the foot angle calculation device according to each example embodiment of the present invention will be described by using an information processing device 90 of FIG. 23 as an example. The information processing device 90 (also referred to as a computer) in FIG. 23 is a configuration example for achieving the foot angle calculation device of each example embodiment, and does not limit the scope of the present invention.

Figure 23:
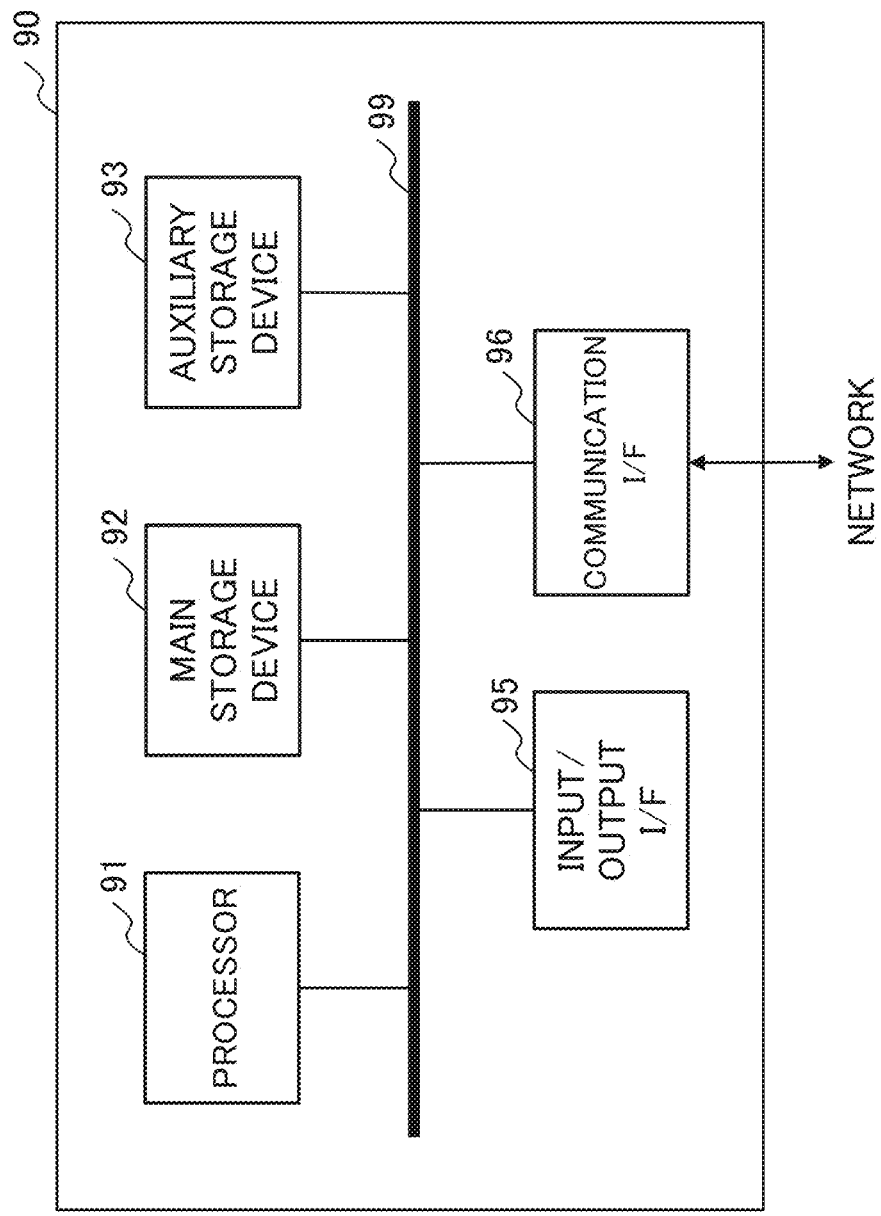
FIG. 23 is a block diagram illustrating an example of a hardware configuration that achieves the foot angle calculation device according to each example embodiment of the present invention.

As illustrated in FIG. 23, the information processing device 90 includes a processor 91, a main storage device 92, an auxiliary storage device 93, an input/output interface 95, and a communication interface 96. In FIG. 23, the interface is abbreviated as an I/F (interface). The processor 91, the main storage device 92, the auxiliary storage device 93, the input/output interface 95, and the communication interface 96 are data-communicably connected to each other via a bus 99. The processor 91, the main storage device 92, the auxiliary storage device 93, and the input/output interface 95 are connected to a network such as the Internet or an intranet via the communication interface 96.

The processor 91 develops the program stored in the auxiliary storage device 93 or the like in the main storage device 92 and executes the developed program. In the present example embodiment, it is sufficient if the configuration is made to use the software program installed in the information processing device 90. The processor 91 executes processing by the foot angle calculation device according to each example embodiment.

The main storage device 92 has an area in which a program is developed. It is sufficient if the main storage device 92 is a volatile memory such as a dynamic random access memory (DRAM). A nonvolatile memory such as a magnetoresistive random access memory (MRAM) may be configured and added as the main storage device 92.

The auxiliary storage device 93 stores various types of data. The auxiliary storage device 93 includes a local disk such as a hard disk or a flash memory. The various types of data may be stored in the main storage device 92, and the auxiliary storage device 93 may be omitted.

The input/output interface 95 is an interface for connecting the information processing device 90 and a peripheral device. The communication interface 96 is an interface for connecting to the external system or device through a network such as the Internet or an intranet based on a standard or a specification. The input/output interface 95 and the communication interface 96 may be shared as an interface connected to an external device.

An input device such as a keyboard, a mouse, or a touch panel may be configured to be connected to the information processing device 90 as necessary. These input devices are used to input information and settings. In a case where the touch panel is used as the input device, it is sufficient if the display screen of a display device also serves as the interface of the input device. It is sufficient if the data communication between the processor 91 and the input device is mediated by the input/output interface 95.

The information processing device 90 may be provided with a display device for displaying information. In a case where the display device is provided, the information processing device 90 preferably includes a display control device (not illustrated) for controlling the display of the display device. It is sufficient if the display device is connected to the information processing device 90 via the input/output interface 95.

The information processing device 90 may be provided with a notification device for notifying information. In a case where the notification device is provided, the information processing device 90 preferably includes a control device (not illustrated) for controlling the notification device. It is sufficient if the notification device is connected to the information processing device 90 via the input/output interface 95.

The information processing device 90 may be provided with a disk drive as necessary. The disk drive is connected to the bus 99. The disk drive mediates reading of data/program from a recording medium, writing of the processing result of the information processing device 90 to the recording medium, and the like between the processor 91 and the recording medium (program recording medium) (not illustrated). The recording medium can be achieved by, for example, an optical recording medium such as a compact disc (CD) or a digital versatile disc (DVD). The recording medium may be achieved by a semiconductor recording medium such as a universal serial bus (USB) memory or a secure digital (SD) card, a magnetic recording medium such as a flexible disk, or another recording medium.

The above is an example of the hardware configuration for achieving the foot angle calculation device according to each example embodiment of the present invention. The hardware configuration of FIG. 23 is an example of the hardware configuration for achieving the foot angle calculation device according to each example embodiment, and does not limit the scope of the present invention. A program for causing a computer to execute processing related to the foot angle calculation device according to each example embodiment is also included in the scope of the present invention. A program recording medium in which the program according to each example embodiment is recorded is also included in the scope of the present invention. The components of the foot angle calculation device of each example embodiment can be randomly combined. The components of the foot angle calculation device of each example embodiment may be achieved by software or may be achieved by a circuit.

While the invention has been particularly shown and described with reference to exemplary embodiments thereof, the invention is not limited to these embodiments. It will be understood by those of ordinary skill in the art that various changes in form and details may be made therein without departing from the spirit and scope of the present invention as defined by the claims.

REFERENCE SIGNS LIST 1, 2, 3, 4 gait measurement system
11, 21, 31, 41 data acquisition device
12, 22, 32, 42 foot angle calculation device
33 display device
45 notification device
111, 211 acceleration sensor
112, 212 angular velocity sensor
113, 213 signal processing unit
115, 215 data transmission unit
121 integration unit
123, 223 posture angle calculation unit
125, 225 foot angle calculation unit
214 integration unit
330 monitor

What is claimed is:

1. A system comprising:
a sensor installed in a shoe at a position at which the sensor faces a back side of an arch of a foot inserted in the shoe, the sensor configured to detect an angular velocity and an acceleration of the foot;
at least one memory storing instructions; and
at least one processor connected to the at least one memory and configured to execute the instructions to:
receive, from the sensor, sensor data including an angular velocity vector and an acceleration vector of the foot;
calculate a velocity vector of the foot portion by using the acceleration vector;
calculate a posture angle by using the angular velocity vector of the foot portion;
calculate a foot angle formed by the velocity vector of the foot portion and a center line of the foot by using the velocity vector and the posture angle; and
output information regarding the calculated foot angle.

2. The system according to claim 1,
the at least one processor is configured to execute the instructions to
calculate the velocity vector by time-integrating the acceleration vector.

3. The system according to claim 1, wherein
the at least one processor is configured to execute the instructions to
calculate the foot angle by using the velocity vector averaged in a swing phase.

4. The system according to claim 3, wherein
the at least one processor is configured to execute the instructions to
calculate the foot angle by using the velocity vector weighted in a mid-swing period included in the swing phase.

5. The system according to claim 1, wherein
the at least one processor is configured to execute the instructions to
output the information regarding the calculated foot angle to a display device.

6. The system according to claim 1, wherein
the at least one processor is configured to execute the instructions to
output the information regarding the calculated foot angle to a notification device.

7. A gait measurement method performed by a system and comprising:
detecting, by a sensor of the system installed in a shoe at a position at which the sensor faces a back side of an arch of a foot inserted in the shoe, an angular velocity and an acceleration of the foot;
receiving, by at least one processor of the system from the sensor, sensor data including an angular velocity vector and an acceleration vector of the foot;
calculating, by the at least one processor, a velocity vector of the foot portion by using the acceleration vector;
calculating, by the at least one processor, a posture angle by using the angular velocity vector of the foot portion;
calculating, by the at least one processor, a foot angle formed by the velocity vector of the foot portion and a center line of the foot by using the velocity vector and the posture angle; and outputting, by the at least one processor, information regarding the calculated foot angle.

8. A non-transitory program recording medium storing a program executable by at least one processor of a system comprising a sensor installed in a shoe at a position at which the sensor faces a back side of an arch of a foot inserted in the shoe, the sensor configured to detect an angular velocity and an acceleration of the foot, the program executable by the at least one processor to perform processing comprising:
   receiving, from the sensor, sensor data including an angular velocity vector and an acceleration vector of the foot;
   calculating a velocity vector of the foot portion by using the acceleration vector;
   calculating a posture angle by using the angular velocity vector of the foot portion;
   calculating a foot angle formed by the velocity vector of the foot portion and a center line of the foot by using the velocity vector and the posture angle; and
   outputting information regarding the calculated foot angle.

* * * * *